US011278455B2

(12) United States Patent
Zelka

(10) Patent No.: US 11,278,455 B2
(45) Date of Patent: Mar. 22, 2022

(54) METHODS FOR MAINTAINING AN ELECTRO-ACTIVE POLYMER IN A PRE-STRETCH STATE

(71) Applicant: ElastiMed Ltd., IP Tradyon (IL)

(72) Inventor: Omer Zelka, Tel-Aviv (IL)

(73) Assignee: ElastiMed Ltd., Yokneam Ilit (IL)

( * ) Notice: Subject to any disclaimer, the term of this patent is extended or adjusted under 35 U.S.C. 154(b) by 419 days.

(21) Appl. No.: 16/066,637

(22) PCT Filed: Jun. 30, 2016

(86) PCT No.: PCT/IB2016/001046
§ 371 (c)(1),
(2) Date: Jun. 27, 2018

(87) PCT Pub. No.: WO2017/115118
PCT Pub. Date: Jul. 6, 2017

(65) Prior Publication Data
US 2019/0015260 A1      Jan. 17, 2019

Related U.S. Application Data

(63) Continuation-in-part of application No. 14/982,645, filed on Dec. 29, 2015, now Pat. No. 9,433,537, and
(Continued)

(51) Int. Cl.
*H01R 9/00* (2006.01)
*H05K 3/00* (2006.01)
(Continued)

(52) U.S. Cl.
CPC ........ *A61F 13/085* (2013.01); *A61B 17/1322* (2013.01); *A61F 5/0127* (2013.01);
(Continued)

(58) Field of Classification Search
CPC ........ A61B 17/1322; A61B 2017/0002; A61B 2017/00402; A61B 2017/00411;
(Continued)

(56) References Cited

U.S. PATENT DOCUMENTS 6,376,971 B1 * 4/2002 Pelrine .................... F04B 35/00
                                                               310/363
6,513,110 B1    4/2003 Pelrine et al.
(Continued)

FOREIGN PATENT DOCUMENTS

| EP | 1645255 A1 | 4/2006 |
|---|---|---|
| JP | 2003-506858 | 2/2003 |

(Continued)

OTHER PUBLICATIONS

International Search Report and Written Opinion from International Application No. PCT/IB2016/001046 dated Nov. 29, 2016.
(Continued)

*Primary Examiner* — Paul D Kim
(74) *Attorney, Agent, or Firm* — Greenberg Traurig, LLP

(57) ABSTRACT

In some embodiments, the present invention is directed to an actuator which includes at least the following: a pre-stretched electro-active polymer film being pre-stretched in a single or biaxial planar directions; at least one first semi-stiff conductor attached to a first surface of the pre-stretched electro-active polymer film, wherein the first surface is parallel to the single or biaxial planar stretch directions; at least one second semi-stiff conductor attached to a second surface of the pre-stretched electro-active polymer film, wherein the second surface is opposite to the first surface; where the semi-stiff conductors are configured to: fix the pre-stretched electro-active polymer film in a pre-stretched state and allow the pre-stretched electro-active polymer film to expand; a pair of mechanical connectors
(Continued)

coupled to each end of an active region of the pre-stretched electro-active polymer film.

20 Claims, 21 Drawing Sheets

Related U.S. Application Data a continuation-in-part of application No. PCT/IB2015/002539, filed on Dec. 29, 2015.

(60) Provisional application No. 62/097,372, filed on Dec. 29, 2014, provisional application No. 62/112,498, filed on Feb. 5, 2015, provisional application No. 62/112,509, filed on Feb. 5, 2015.

(51) Int. Cl.

| | | |
|---|---|---|
| *A61F 13/08* | (2006.01) | |
| *A61B 17/132* | (2006.01) | |
| *B29C 53/04* | (2006.01) | |
| *A61F 5/01* | (2006.01) | |
| *B29C 55/14* | (2006.01) | |
| *A61B 17/00* | (2006.01) | |
| *B29K 33/00* | (2006.01) | |
| *B29K 83/00* | (2006.01) | |
| *B29L 31/48* | (2006.01) | |
| *B29C 55/12* | (2006.01) | |
| *A61B 90/00* | (2016.01) | |
| *A61F 2/50* | (2006.01) | |
| *B29L 31/00* | (2006.01) | |

(52) U.S. Cl.
CPC .... *B29C 53/04* (2013.01); *A61B 2017/00022* (2013.01); *A61B 2017/00402* (2013.01); *A61B 2017/00411* (2013.01); *A61B 2017/00526* (2013.01); *A61B 2017/00862* (2013.01); *A61B 2017/00871* (2013.01); *A61B 2090/064* (2016.02); *A61F 2/50* (2013.01); *A61F 5/0102* (2013.01); *A61F 13/08* (2013.01); *A61F 2002/5066* (2013.01); *A61F 2005/0155* (2013.01); *B29C 55/12* (2013.01); *B29C 55/14* (2013.01); *B29K 2033/08* (2013.01); *B29K 2083/00* (2013.01); *B29K 2995/0006* (2013.01); *B29L 2031/48* (2013.01); *B29L 2031/753* (2013.01)

(58) Field of Classification Search
CPC ........... A61B 2017/00526; A61B 2017/00862; A61B 2017/00871; A61B 2090/064; B29K 2995/0006; B29K 2083/00; B29K 2033/08; B29C 53/04; B29C 55/12; B29C 55/14; B29L 2031/48; B29L 2031/753; A61F 5/0102; A61F 5/0127; A61F 2005/0155; A61F 2/50; A61F 2002/5066; A61F 13/08; A61F 13/085
See application file for complete search history.

(56) References Cited

U.S. PATENT DOCUMENTS

| | | | |
|---|---|---|---|
| 6,543,110 B1 | 4/2003 | Pelrine et al. | |
| 6,812,624 B1 | 11/2004 | Pei et al. | |
| 7,034,432 B1* | 4/2006 | Pelrine | F02G 1/043 310/309 |
| 7,038,357 B2 | 5/2006 | Goldenberg et al. | |
| 7,518,284 B2* | 4/2009 | Benslimane | B81B 3/007 310/311 |
| 7,732,999 B2* | 6/2010 | Clausen | H01L 41/0986 310/369 |
| 7,826,017 B2 | 11/2010 | Uesaka | |
| 7,868,221 B2 | 1/2011 | Munch-Fals et al. | |
| 7,880,371 B2* | 2/2011 | Benslimane | H01L 41/27 310/367 |
| 7,898,620 B2 | 3/2011 | Ikeda et al. | |
| 2005/0040733 A1 | 2/2005 | Goldenberg et al. | |
| 2005/0046313 A1 | 3/2005 | Basheer et al. | |
| 2005/0157893 A1 | 7/2005 | Pelrine et al. | |
| 2006/0238079 A1 | 10/2006 | Pei et al. | |
| 2007/0114885 A1 | 5/2007 | Benslimane et al. | |
| 2007/0116858 A1* | 5/2007 | Benslimane | H01L 41/45 427/58 |
| 2008/0180875 A1 | 7/2008 | Biggs et al. | |
| 2008/0292827 A1 | 11/2008 | Lee | |
| 2010/0109486 A1 | 5/2010 | Polyakov et al. | |
| 2011/0198971 A1 | 8/2011 | Tryson et al. | |
| 2012/0169184 A1 | 7/2012 | Pelrine et al. | |
| 2013/0175898 A1 | 7/2013 | Brokken et al. | |
| 2013/0176608 A1 | 7/2013 | Brokken et al. | |
| 2013/0207510 A1 | 8/2013 | Poole et al. | |
| 2013/0345610 A1 | 12/2013 | Larson et al. | |
| 2014/0091857 A1* | 4/2014 | Bernstein | G06F 3/0202 327/517 |
| 2015/0040733 A1 | 2/2015 | Croft | |
| 2016/0338207 A1* | 11/2016 | Zelka | H01L 41/0478 |

FOREIGN PATENT DOCUMENTS

| | | |
|---|---|---|
| JP | 2006-520180 A | 8/2006 |
| JP | 2007-510285 A | 4/2007 |
| JP | 2008-515502 A | 5/2008 |
| JP | 2009-523043 A | 6/2009 |
| JP | 2011-83122 A | 4/2011 |
| JP | 2011-234529 A | 11/2011 |
| JP | 2012-523809 A | 10/2012 |
| JP | 2013-539343 A | 10/2013 |
| JP | 2013-230356 A | 11/2013 |
| JP | 2014-507930 A | 3/2014 |
| WO | 01/06579 A2 | 1/2001 |
| WO | 2001006579 A2 | 1/2001 |
| WO | 2005081676 A2 | 9/2005 |
| WO | 2006123317 A2 | 11/2006 |
| WO | 2007079777 A1 | 7/2007 |
| WO | 2008052561 A1 | 5/2008 |
| WO | 2013120493 A1 | 8/2013 |
| WO | 2014199167 A1 | 12/2014 |

OTHER PUBLICATIONS

Pourazadi et al., "On the design of a DEA-based device to potentially assist lower leg disorders: an analytical and FEM investigation accounting for nonlinearities of the leg and device deformations"; BioMed Engineering OnLine (2015) 14:103.

Extended European Search Report (EP 15875312.9) dated Jul. 18, 2018, 10 pages.

* cited by examiner

METHODS FOR MAINTAINING AN ELECTRO-ACTIVE POLYMER IN A PRE-STRETCH STATE

RELATED APPLICATIONS

This application is a continuation-in-part of International Appln. No. PCT/IB2015/002539, filed Dec. 29, 2015, entitled "METHODS AND MECHANISMS FOR MAINTAINING AN ELECTRO-ACTIVE POLYMER IN A PRE-STRETCH STATE AND USES THEREOF," and a continuation-in-part of U.S. patent application Ser. No. 14/982,645, filed Dec. 29, 2015, entitled "METHODS AND MECHANISMS FOR MAINTAINING AN ELECTRO-ACTIVE POLYMER IN A PRE-STRETCH STATE AND USES THEREOF," which are both claim the priority of U.S. provisional patent application No. 62/097,372; filed Dec. 29, 2014; entitled "METHODS AND MECHANISMS FOR MAINTAINING AN ELECTRO-ACTIVE POLYMER IN A PRE-STRETCH STATE," U.S. Provisional Application No. 62/112,498; filed Feb. 5, 2015; entitled "METHODS AND MECHANISMS FOR MAINTAINING AN ELECTRO-ACTIVE POLYMER FILM IN A PRE-STRETCH STATE BY WRAPPING IT AROUND A SOLID BODY," and U.S. Provisional Application No. 62/112,509; filed Feb. 5, 2015; entitled "ELECTRO-ACTIVE POLYMER BASED COMPRESSION BANDAGE." All of above identified priority patent applications are incorporated herein by reference in their entirety for all purposes.

TECHNICAL FIELD

In some embodiments, the present invention relates to methods and mechanisms thereof for maintaining electro-active polymers film in a pre-stretch state.

BACKGROUND

Typically, electro-active polymers are polymers that exhibit a change in size or shape when stimulated by an electric field.

BRIEF SUMMARY

In some embodiments, the present invention is directed to a method that at least includes one or more of the following steps of: a) mechanically pre-stretching an electro-active polymer film in a single or biaxial directions to form a pre-stretched electro-active polymer film; b) attaching a first semi-stiff conductor to a first surface of the electro-active polymer film and a second semi-stiff conductor to a second surface, each semi-stiff conductor is configured to fix the electro-active polymer film in a pre-stretched state; and c) coupling a pair of mechanical connectors at each end of the active region.

In some embodiments, in order to maintain the electro-active polymer film in pre-stretch state on a single axis, a stretchable conductor is attached to the electro-active polymer (EAP) film which is, then, wrapped around a solid body. In some embodiments, the EAP actuator can be covered on at least one side of the film by an isolating layer, which is configured to resist the voltage that is applied on the EAP film. In some embodiments, the isolating layer can prevent voltage breakthrough from the EAP actuator and the solid body.

In some embodiments, the required pre-stretch in a single axis of the EAP film can be determined by a visual indicator, e.g. a hills and valley pattern with a solid strap or by pre-arranged guide lines or any other kind of visual indicator. In some embodiments, after pre-stretching the electro-active polymer film and attaching at least one stretchable conductor, the film is attached to a solid mechanism that fixes the film in a pre-stretch state in a single axis, while allowing it to expand and be wrapped around a solid body on the other axis. In some embodiments, the solid mechanism can be parallel solid plastic straps attached to the electro active polymer film. In some embodiments, the plastic straps used to fix the pre-stretched film in a single axis, can also be used to prevent the film from contracting in the other axis, by attaching holders that keep the plastic straps at a minimal distance, while allowing them to expand. In some embodiments, the attachment of the solid mechanism can be made by gluing and/or any other similarly method(s) of attachment.

In some embodiments, the attaching of a conductor is performed by at least one methodology selected from the group consisting of printing, etching, brushing, water dispersion, gluing, and any combination thereof. In some embodiments, the instant method further includes: folding the electro-active polymer X times, wherein X is between 2 and 10,000. In some embodiments, the conductor is selected from the group consisting of a stretchable conductor, a rigid conductor in an expanding pattern, a printed conductor in an expanding pattern and any combination thereof. In some embodiments, the printed conductor is made from at least one of a conducting silver ink, a conducting carbon ink, and any combination thereof. In some embodiments, the stretchable conductor is made from networks of gold or carbon nano-particles embedded in elastic polyurethane. In some embodiments, the stretchable conductor is made from carbon graphite powder with silicon oil, conducting silicon grease, Polyaniline (PAni) based solution, carbon black powder, conducting polymer, conductive rubber and any combination thereof. In some embodiments, the expanding pattern is one of a zigzag pattern, and expanding diamond pattern.

In some embodiments, in order to maintain the electro-active polymer film in pre-stretch state, the electro-active polymer film is fixed to two or more circular frames. In some embodiments, the frames are held with a gap between them, allowing the electro-active polymer film to curve between the frames, in a radial direction. Electrical activation of the electro-active polymer film, creates contraction in a radial direction.

In some embodiments, the present invention is directed to an actuator that at least includes: a) at least one active region, having at least one electro-active polymer layer; b) at least two conducting layers arranged on the surface of the electro-active polymer layer such that each conducting layer is attached on each surface side of the electro-active polymer layer in an expanding pattern after pre-stretching of the electro-active polymer layer, thereby maintaining the electro-active polymer layer in a pre-stretched state; and c) a pair of mechanical connectors at either end of the active region, wherein a positive connector is operably connected to one end of the at least one active region, and a negative connector is operably connected to the other end of the at least one active region.

In some embodiments, the actuator further includes at least one strain measuring mechanism for monitoring strain feedback for the at least one active region, whereby turning the actuator into a transducer, meaning that mechanically stretching the actuator, creates an electric charge. In some embodiments, measuring the strain is based on measuring the electric charge or measuring the actuator's capacitance while stretching and contracting the actuator. In some embodiments, the actuator further includes at least one strain measuring mechanism for monitoring strain feedback for the at least one active region, whereby measuring the capacitance of the actuator can be translated to measuring the actuator's strain. In some embodiments, the electro-active polymer layer is mechanically pre-stretched during a fabrication. In some embodiments, the expanding pattern is a zigzag pattern. In some embodiments, each conducting layer is a stretchable conductor. In some embodiments, a thickness of the electro-active polymer layer is between 10 um-5 mm. In some embodiments, the electro-active polymer is folded. In some embodiments, each conducting layer is printed or etched to the electro-active polymer.

In some embodiments, the EAP actuator can be used for the construction of an active compression bandage, including of: a bandage, which is placed on a body part of an animal or a human being. For example, in the case of human, the active compression bandage can be placed on, for example, but not limited to, a leg, a calf, a foot, a hand or an arm. For example, the bandage is fixed on the body part, by using between 1 to 20 elastic straps, which are wrapped around the body part, and are connected to the bandage by Velcro, clip-on buttons, buttons, zipper, sewing or any other similar fixation method. In some embodiments, the elastic straps are stretched when wrapped around the body part. In some embodiments, the bandage and the elastic straps are threaded with EAP actuators. In some embodiments, by stretching the elastic straps, the EAP actuators are pre-stretched, and, then, are fixed in a pre-stretch state.

In some embodiments, the bandage is connected to a control box, which activates and controls the EAP actuators activation. In some embodiments, the control box at least includes: a battery or a connection to a power socket and an electrical circuit, which transforms the battery or the connection to a power socket output voltage to the required voltage for the EAP and activates and de-activates the EAP actuators, by applying voltage on each actuator, separately or simultaneously, according to a pre-determined sequence. In some embodiments, the control box can also measure the expansion of the EAP actuator.

BRIEF DESCRIPTION OF THE DRAWINGS

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DETAILED DESCRIPTION

Figure 1:
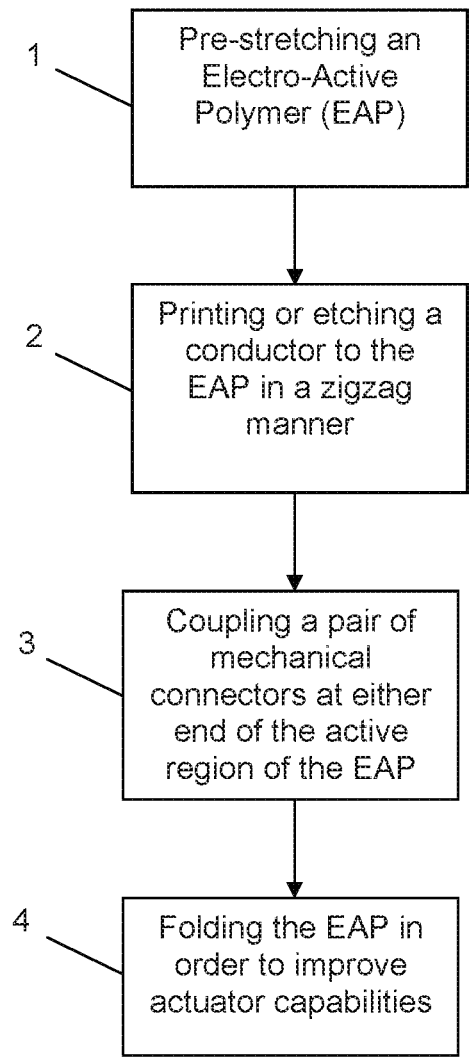
FIG. 1 is a flow chart generally illustrating an exemplary procedure for maintaining an electro-active polymer in a pre-stretch state, according to some embodiments of the present invention.

Reference will now be made to several embodiments of the present invention(s), examples of which are illustrated in the accompanying figures. Wherever practicable similar or like reference numbers may be used in the figures and may indicate similar or like functionality. The figures depict embodiments of the present invention for purposes of illustration only. One skilled in the art will readily recognize from the following description that alternative embodiments of the structures and methods illustrated herein may be employed without departing from the principles of the invention described herein. The terms, "for example", "e.g.", "optionally", as used herein, are intended to be used to introduce non-limiting examples.

The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

Throughout this description the term "Electro-Active Polymer," "electro-active polymer" or "EAP" is used to indicate dielectric elastomer film(s) adapted to be stretched biaxially or in a single axis. The use of the term "EAP" is a general descriptive of a genus and should not be limited to any particular shape, construction material and/or geometry, and at least some embodiments of the present invention cover are directed to all suitable elastic materials, such as the 3M™ VHB™ 4910, 4905, 4955, 4959 or 9460 Tape, Hi-Bond™ VST4050 Foamed acrylic tape, Dow Corning™ or Nusil™ silicon elastomer, Elastosil or Silpuran film by Wacker, or any other suitable silicon or acrylic dielectric elastomer.

As used herein, a "conductor" refers to an object or type of material that allows the flow of electrical current in one or more directions.

In some embodiments, the present invention provides a method for keeping the electro-active polymer film in a pre-stretched state/condition on a single axis, by wrapping and fixing it around a solid body, e.g. a human body part.

In some embodiments, the instant method of the present invention at least includes: a) mechanically pre-stretching an electro-active polymer film in a single or biaxial directions to form a pre-stretched electro-active polymer film; b) attaching a semi-stiff conductor to both surfaces of the electro-active polymer film, the semi-stiff conductor is configured to fix the electro-active polymer film in a pre-stretched state; and c) coupling a pair of mechanical connectors at each end of the active region.

In some embodiments, the attaching is performed by at least one methodology selected from the group consisting of printing, etching, brushing, water dispersion, gluing, and any combination thereof. In some embodiments, the instant method further includes: folding the electro-active polymer X times, wherein X is between 2 and 10,000. In some embodiments, the conductor is selected from the group consisting of a stretchable conductor, a rigid conductor in an expanding pattern, a printed conductor in an expanding patter and any combination thereof.

In some embodiment, said conductor might be a stretchable conductor, for example but not limited by, carbon or silver based conducting ink, Polyaniline (PAni) based solution, carbon based solution, carbon black powder, conducting polymer, conductive rubber, conductive silver or carbon paste, conductive epoxy, conducting grease, laser cut or molded rigid conducting sheet in an expanding pattern, graphite powder based solution, stretchable conducting sheet made by networks of gold and/or carbon nano-particles embedded in elastic polyurethane or any combination thereof. In some embodiment, said conductor might be attached to the EAP film by, for example but not limited to, printing, etching, brushing, water or organic or non-organic solvent or surfactant dispersion or any other type of spray or aerosol, gluing and/or any other similarly suitable method(s) of attachment or any combination thereof.

In some embodiment, the inventive EAP film of the present invention can be used as a compression device or force feedback device.

In some embodiments, the stretchable conductor is made from carbon black powder. In some embodiments, the stretchable conductor is made from a conductive polymer. In some embodiments, the stretchable conductor is made from conductive rubber. In some embodiments, the expanding pattern is one of a zigzag pattern, and expanding diamond pattern.

In some embodiments, the instant actuator of the present invention at least includes: a) at least one active region, having at least one electro-active polymer layer; b) at least two conducting layers arranged on the surface of the electro-active polymer layer such that each conducting layer is attached on each surface side of the electro-active polymer layer in an expanding pattern after pre-stretching of the electro-active polymer layer, thereby maintaining the electro-active polymer layer in a pre-stretched state; and c) a pair of mechanical connectors at either end of the active region, wherein a positive connector is operably connected to one end of the at least one active region, and a negative connector is operably connected to the other end of the at least one active region.

In some embodiments, the actuator further includes at least one strain measuring mechanism for monitoring strain feedback for the at least one active region, whereby turning the actuator into a transducer, meaning that mechanically stretching the actuator, creates an electric charge. In some embodiments, measuring the strain is based on measuring the electric charge while stretching and contracting the actuator. In some embodiments, the exemplary actuator further includes at least one strain measuring mechanism for monitoring strain feedback for the at least one active region, whereby measuring the capacitance of the actuator can be translated to measuring the actuator's strain. In some embodiments, the electro-active polymer layer is mechanically pre-stretched during a fabrication. In some embodiments, the expanding pattern is a zigzag pattern. In some embodiments, each conducting layer is a stretchable conductor. In some embodiments, a thickness of the electro-active polymer layer is between 10 um-5 mm. In some embodiments, the electro-active polymer is folded. In some embodiments, the electro-active polymer actuator is constructed from multiple layers of electro-active polymer films attached to one another. In some embodiments, the method to attach the layers of electro-active polymer film, is made by gluing or any other method of attachment. In some embodiments, each conducting layer is printed or etched to the electro-active polymer.

In some embodiments, the present invention provides a method for keeping the electro-active polymer in a pre-stretched state/condition by coating the electro-active polymer with a stiffened material such as, but not limited to, a semi-stiff or stretchable conductor layer on both sides, and utilizing the semi-stiff conductor in a zigzag pattern or any other suitable expanding method, such as, but not limited to, the networks of gold or carbon nano-particles embedded in elastic polyurethane on the surface of the electro-active polymer.

In some embodiments, the present invention provides electro-active polymers, transducers and/or devices that maintain pre-stretch condition in one or more portions of an electro-active polymer. In some embodiments, electro-active polymers described herein includes a pre-stretched portion and at least one conductor configured to maintain the pre-stretch condition in the pre-stretched portion. In some embodiments, an exemplary conductor is in a form of a semi-stiff conductor made, for example but not limited to, by a conducting ink (e.g., silver and/or carbon based conductive ink, for example Creative Materials, Inc. 125-10 silver based electrically conductive ink (http://www.creativematerials-.com/data-sheets/page-4/) or Creative Materials, Inc. 112-48 carbon based conductive ink) (http://www.creativemateri-als.com/data-sheets/). In some embodiments, the exemplary conductor is in a form of a stretchable conductor, such as, for example, a stretchable electrical conductor that is created out of networks of gold and/or carbon nano-particles embedded in elastic polyurethane. In some embodiments, the exemplary conductor is made from a carbon black powder layer attached to the electro-active polymer, for example but not limited to, Ketjenblack EC-600JD powder by Akzo Nobel, Super C65 by C-Nergy or 250P by Enscao. In some embodiments, the exemplary conductor is made from carbon or silver paste, for example but not limited to WIK20489-56A by Henkel. In some embodiments, the exemplary conductor is made from carbon or silver conductive epoxy, for example but not limited to H20E by Epo-Teck. In some embodiments, the exemplary conductor is made by Polyaniline (PAni) based solution, carbon-based solution, a laser cut or molded rigid conducting sheet, or any combination thereof.

The term "pre-stretch," and its variants are being used herein to describe mechanically stretching of an electro-active polymer film in a single axis or biaxial planar direction prior to activation. In some embodiments, by maintaining the EAP in the pre-stretch state/condition, the instant invention allows to at least:

i) enhance the electrical breakdown strength,
ii) minimize or eliminate pull-in instability; and/or
iii) decrease the EAP film's thickness, thus requiring a lower voltage to obtain the same electrostatic pressure.

In some embodiments, the term "pre-stretch" is referred to any mechanical stretch from 10%-5000% of the electro-active polymer film original size. In some embodiments, the "pre-stretch" is referred to any mechanical stretch from 10%-100% of the electro-active polymer film original size. In some embodiments, the term "pre-stretch" is referred to any mechanical stretch from 50%-100% of the electro-active polymer film original size. In some embodiments, the term "pre-stretch" is referred to any mechanical stretch from 50%-1000% of the electro-active polymer film original size. In some embodiments, the term "pre-stretch" is referred to any mechanical stretch from 100%-5000% of the electro-active polymer film original size. In some embodiments, the term "pre-stretch" is referred to any mechanical stretch from 1000%-5000% of the electro-active polymer film original size. In some embodiments, the term "pre-stretch" is referred to any mechanical stretch from 2500%-5000% of the electro-active polymer film original size.

In some embodiments, the ratio in the biaxial pre-stretch on the electro-active polymer film, between pre-stretch on X axis and Y axis, can affect the amount of expansion created by the electric field, in each axis. For example, in some embodiments, pre-stretching 3M VHB 4905 film by 2.5 on the X axis, and by 2 on the Y axis, will create a larger expansion due to electrical activation on the Y axis of the film, than when pre-stretching the film by 2 on the X axis, and by 2.5 on the Y axis. In some embodiments, certain configurations, can reverse the activation direction of the electro-active polymer actuator (for example, pre-stretching 3M VHB 4905 film by 2.5 on the X axis, and by 2 on the Y axis, and wrapping it around a solid body as the X axis of the film is in the peripheral direction, will cause the actuator to contract in a radial direction, due to electrical activation. Pre-stretching the film by 2 on the X axis, and by 2.5 on the Y axis, and wrapping it around a solid body as the X axis of the film is in the peripheral direction, will cause the actuator to contract in a radial direction, due to electrical deactivation).

In some embodiments, the exemplary conductor fixes the pre-stretch portion in the pre-stretch condition, while allowing the electro-active polymer to change size in a specific direction or directions. In some embodiments, the exemplary conductor, discussed herein, is a conductor that is sufficiently stiff to fix the EAP in a pre-stretch state, while allowing the EAP to expand. In some embodiments, the change in size of the EAP is due to an exemplary method of attaching the exemplary conductor on the EAP in accordance with some embodiments of the present invention and not due to a characteristic of the exemplary conductor itself.

In some embodiments, the present invention provides electro-active polymers, transducers and/or devices that maintain a pre-stretch state/condition in one or more portions of an electro-active polymer. In some embodiments, electro-active polymers described herein include at least one pre-stretched portion attached to at least one conductor which is configured to maintain the electro-active polymer film in the least one pre-stretched portion in the pre-stretch state/condition.

In some embodiments, an exemplary conductor utilized by the present invention can be a semi-stiff conductor or a stretchable conductor. In some embodiments, the exemplary conductor utilized by the present invention can fix the electro-active polymer film in the pre-stretch state/condition, while allowing the electro-active polymer to change size in a specific direction or directions.

In some embodiments, in order to maintain the electro-active polymer film in pre-stretch state, the electro-active polymer film is fixed to two or more circular frames. In some embodiments, the frames are held with a gap between them, allowing the electro-active polymer film to curve between the frames, in a radial direction. Electrical activation of the electro-active polymer film, creates contraction in a radial direction. In some embodiments, the circular frames can be made from, but not limited to, a conveyor chain, bicycle chain, roller chain or any other type of chain, which is wrapped around a solid body. In some embodiments, the ratio in the biaxial pre-stretch on the electro-active polymer film, prior to attaching the film to the circular frame, can affect the direction of electrical activation (for example, pre-stretching 3M VHB 4905 film by 2.5 on the X axis, and by 2 on the Y axis, before attaching the film to the circular frame as the X axis of the film is in the peripheral direction, will cause the actuator to contract in a radial direction, due to electrical activation. Pre-stretching the film by 2 on the X axis, and by 2.5 on the Y axis, before attaching the film to the circular frame, as the X axis of the film is in the peripheral direction, will cause the actuator to contract in a radial direction, due to electrical deactivation)

In some embodiments, the present invention is directed to a method for maintain an electro-active polymer film in a pre-stretched state, where the method at least includes the steps of:

i) pre-stretching the electro-active polymer film, by mechanically stretching the film in a single or biaxial directions;

ii) attaching at least one conductor to at least one surface of the electro-active polymer film, by, for example but not limited to, printing, etching, brushing, water dispersion, gluing and/or any other similarly suitable method(s) of attachment;

iii) attaching part of the electro-active polymer film to the outer plate of a roller chain;

iv) wrapping the roller chain around a solid body;

In some embodiments, the present invention is directed to a method for maintain an electro-active polymer film in a pre-stretched state, where the method at least includes the steps of:

i) pre-stretching the electro-active polymer film, by mechanically stretching the film in a single or biaxial directions;

ii) attaching at least one conductor to at least one surface of the electro-active polymer film, by, for example but not limited to, printing, etching, brushing, water dispersion, gluing and/or any other similarly suitable method(s) of attachment;

iii) where the at least one conductor has semi-stiff properties (e.g., the conductor enables the electro-active polymer to expand);

iv) maintaining conductivity of at least one conductor at a level of at least 0.1% of its original conductivity, while the at least one conductor being stretched for more than 5%; and v) mechanically fixing the electro-active polymer film being in a pre-stretched state.

In some embodiments, the exemplary method of the present invention further includes using more than one layer and up to 10,000 layers of electro-active polymer films in order to improve, for example, strength (e.g., allowing the activation based on application of sufficiently strong forces) and/or durability (e.g., minimizing physical damage (e.g., tear).

In some embodiments, the exemplary method of the present invention further includes using more than one layer and up to 1,000 layers of electro-active polymer films in order to improve strength and/or durability of the actuator. In some embodiments, the exemplary method of the present invention further includes using more than one layer and up to 100 layers of electro-active polymer films in order to improve strength and/or durability of the actuator.

In some embodiments, multi-layered structure(s) of electro-active polymer films of the present invention is/are made by, for example but not limited to, folding a single film, attaching multiple films to each other, and/or any combination thereof.

In some embodiments, the exemplary semi-stiff conductor utilized in accordance with the present invention is selected from the group consisting of a stretchable conductor, a rigid conductor in an expanding pattern, a printed conductor in an expanding pattern, and any combination thereof.

In some embodiments, the exemplary stretchable conductor utilized in accordance with the present invention can be created out of networks of gold and/or carbon nano-particles embedded in elastic polyurethane, or any other suitable stretchable conductor.

In some embodiments, the exemplary stretchable conductor utilized in accordance with the present invention can be created by a layer of carbon black powder glued to the electro-active polymer or any other suitable stretchable conductor.

In some embodiments, the exemplary stretchable conductor utilized in accordance with the present invention can be created by a conducting polymer or any other suitable stretchable conductor.

In some embodiments, the exemplary stretchable conductor utilized in accordance with the present invention can be created by a conducting rubber or any other suitable stretchable conductor.

In some embodiments, the exemplary stretchable conductor utilized in accordance with the present invention can be created by applying a carbon or silver paste or any other suitable stretchable conductor.

In some embodiments, the exemplary stretchable conductor utilized in accordance with the present invention can be created by applying a carbon or silver epoxy or any other suitable stretchable conductor.

In some embodiments, the exemplary rigid conductor utilized in accordance with the present invention can be created by laser cutting, molding and/or etching a solid conductor, for example, but not limited to, copper or stainless steel sheet foil. In some embodiments, the exemplary printed conductor utilized in accordance with the present can be a made utilizing a conducting ink based on silver and/or carbon.

In some embodiments, an exemplary expanding pattern utilized in accordance with the present invention refers to one of a zigzag pattern, an expanding diamond pattern or any other suitable expanding pattern.

In some embodiments, the attachment of an exemplary conductor to an electro-active polymer is done by printing, etching, brushing, water or organic solvent and surfactant dispersion, gluing, ion-attachment and/or any other suitable method of the attachment.

In some embodiments, an exemplary actuator can be activated by applying an electric charge on the conducting layers attached to the electro-active polymer film, thus creating an electric field between the conducting layers. The electric field, creates a force, which pulls the conducting layers to each other, thus squeezing the polymer film, which expands in a single axis or biaxial direction. In some embodiments, the activation creates an expansion of the exemplary actuator by 3%-100% in a single axis or biaxial directions from its original size. In some embodiments, the activation creates an expansion of the exemplary actuator by 3%-500% in a single axis or biaxial directions from its original size. In some embodiments, the activation creates an expansion of the exemplary actuator by 3%-1000% in a single axis or biaxial directions from its original size. In some embodiments, the activation creates an expansion of the exemplary actuator by 50%-1000% in a single axis or biaxial directions from its original size. In some embodiments, the activation creates an expansion of the exemplary actuator by 100%-1000% in a single axis or biaxial directions from its original size. In some embodiments, the activation creates an expansion of the exemplary actuator by 500%-1000% in a single axis or biaxial directions from its original size.

In some embodiments, variables that affect the expansion and the direction of the expansion include, but are not limited to:

i) an amount and/or a direction of the pre-stretch;
ii) an electrical charge being applied (e.g., between 1V-20,000V, between 100V-20,000V, between 1000V-20,000V, between 1V-1,000V, between 10V-10,000V, between 10,000V-20,000V);
iii) a method and/or a type of fixation/attachment; and
iv) any combination thereof.

In some embodiments, the methods of the present invention utilize at least one actuator that includes at least the following components:

A. at least one active region, having at least one electro-active polymer layer;

B. at least two conducting layers arranged on the surface of the at least one electro-active polymer layer such that each conducting layer is attached on each surface side of the at least one electro-active polymer layer in an expanding pattern after pre-stretching of the at least one electro-active polymer layer, thereby maintaining the at least one electro-active polymer layer in a pre-stretched state; and C. a pair of mechanical connectors at either end of the at least one active region, wherein a positive connector is operably connected to one end of the at least one active region, and a negative connector is operably connected to the other end of the at least one active region.

In some embodiments, the exemplary actuator in accordance with the present invention further includes at least one component configured for monitoring strain, whereby the exemplary actuator acts as a transducer, i.e., the mechanically stretching of the actuator results in generating an electric charge. In some embodiments, amount of the electrical charge being generated depends on at least the following, but not limited to, amount of stress being applied on the actuator and thus can be used as a stretch, force and/or bend sensor.

In some embodiments, the exemplary actuator in accordance with the present invention further includes at least one component configured for monitoring strain, whereby measuring the capacitance of the actuator can be translated to measuring the actuator's strain. In some embodiments, amount of the change in the capacitance of the actuator depends on at least the following, but not limited to, amount of stress being applied on the actuator and thus can be used as a stretch, force and/or bend sensor.

In some embodiments, the exemplary actuator includes at least one strain measuring mechanism for monitoring strain feedback for the at least one active region whereby acting as a transducer.

In some embodiments, the electro-active polymer film can be pre-stretched:

1) during fabrication, and/or
2) prior or after to the attachment of the semi-stiff or stretchable conductor.

In some embodiments, the pre-stretch condition is reached by utilizing any suitable physical mechanisms that stretch the electro-active polymer film in a single axis or biaxial directions.

In some embodiments, the exemplary expanding pattern, but not limited to, is a zigzag pattern (see FIGS. 2 and 3) that is utilized to attach each conducting layer to the surface of the corresponding electro-active polymer layer. In some embodiments, the exemplary expanding pattern, but not limited to, is any other expanding pattern (e.g., an expanding diamond pattern shown in FIG. 4). In some embodiments, the expanding mechanism that each conducting layer is attached to the surface of the electro-active polymer layer is applied by a stretchable conductor (e.g., the stretchable conductor created out of networks of gold and/or carbon nano-particles embedded in elastic polyurethane; any other suitable stretchable conductor).

In some embodiments, the electro-active polymer film layer has thickness between 10 um-5 mm. In some embodiments, the electro-active polymer film layer has thickness between 100 um-5 mm. In some embodiments, the electro-active polymer film layer has thickness between 1000 um-5 mm. In some embodiments, the electro-active polymer film layer has thickness between 10 um-1 mm. In some embodiments, the electro-active polymer film layer has thickness between 100 um-1 mm. In some embodiments, the electro-active polymer film layer has thickness between 500 um-1 mm.

In some embodiments, each conducting layer is attached to the electro-active polymer layer by, for example but not limited to, at least one of printing (e.g., utilizing conductive ink), etching (e.g., using a solution of electrolyte), brushing (e.g., using carbon graphite powder with silicon oil), water or organic solvent and surfactant dispersion (e.g., using PAni or carbon black based solution), gluing (e.g., gluing a laser cut or molded into an expanding pattern such as zigzag, rigid conducting sheet), and any other suitable applicable method(s).

For example, the organic carbon-black-based solvent can include carbon black dispersed in a mixture of ethyl acetate and Acetone; and can optionally included one or more surfactants.

In some embodiments, electro-active polymers that are pre-stretched improve conversion between electrical and mechanical energy. In some embodiments, the pre-stretch state/condition stabilizes the actuation of the electro-active polymer due to at least one of:

i) minimizing or eliminating the pull-in instability by generating electrostriction (the pull-in instability identifies a state, when voltage is applied on an electro-active polymer film, causing the film to thin down—e.g., voltage produces a higher electric field, which squeezes the electro-active polymer film as a positive feedback until an electrical breakdown, based on calculations described in "Pull-in and wrinkling instabilities of electroactive dielectric actuators," J. Phys. D: Appl. Phys. 43 (2010) 325501, and in Li, et al., "Effect of mechanical pre-stretch on the stabilization of dielectric elastomer actuation," J. Phys. D: Appl. Phys. 44 (2011) 155301, whose this specific disclosure is hereby incorporated herein by reference;

ii) improving the breakdown strength, and iii) reducing the films thickness, which consequently lowers the voltages required for activation. (for example, the voltage required to activated 3M VHB 4910 film, is 50 KV per 1 mm. pre-stretching the film biaxially by 10, reduces the film thickness to 0.1 mm and the activation voltage to 5 KV). For example, in some embodiments, when pre-stretched, acrylic copolymer elastomers (e.g., VHB 4910 or VHB 4905 by 3M Corporation) produce a stable comparatively high and reversible electromechanical stretch of 3% to 1000% in area of the linear stretch.

In the drawings:

FIG. 1 is a flow chart generally illustrating an exemplary procedure for maintaining an electro-active polymer in the pre-stretch state/condition, according to some embodiments of the present invention. In some embodiments, this procedure can include at least the steps of:

i) mechanically and biaxially pre-stretching an electro-active polymer film (step 1);

ii) attaching the electro-active polymer with semi-stiff conductor by one of the following ways, but not limited to: printing (e.g., conducting ink), etching (e.g. by using a solution of electrolyte), brushing (e.g. using carbon graphite powder with silicon oil), water dispersion (e.g. using PAni based solution), gluing (e.g. gluing a laser cut or molded into an expanding pattern such as zigzag or expanding diamond pattern, rigid conducting sheet), or any other suitable attachment method(s) (step 2);

iii) coupling a pair of mechanical connectors at either end of the active region of the electro-active polymer (step 3); and iv) optionally, folding the electro-active polymer in order to improve capabilities of an actuator (i.e., the electro-active polymer with the attached conductor) (step 4).

In some embodiments, by coating the electro-active polymer with a semi-stiff conductor layer from both sides and arranging the conductor in a zigzag pattern (or any other suitable expanding pattern), the method(s) of the present invention allows the electro-active polymer to expand linearly while keeping the pre-stretch state.

Figure 2:
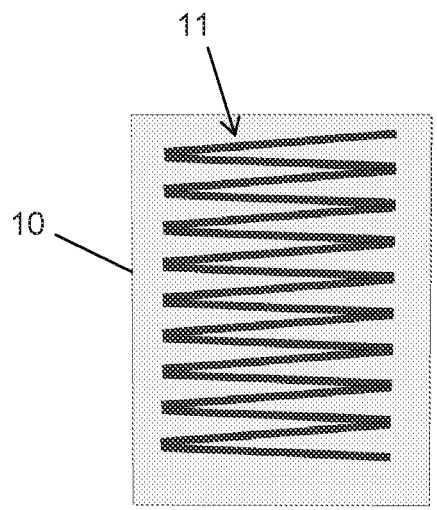
FIG. 2 schematically illustrates an exemplary pre-stretched electro-active polymer, printed or etched with a conductor in a zigzag pattern, according to some embodiments of the present invention.
Figure 3:
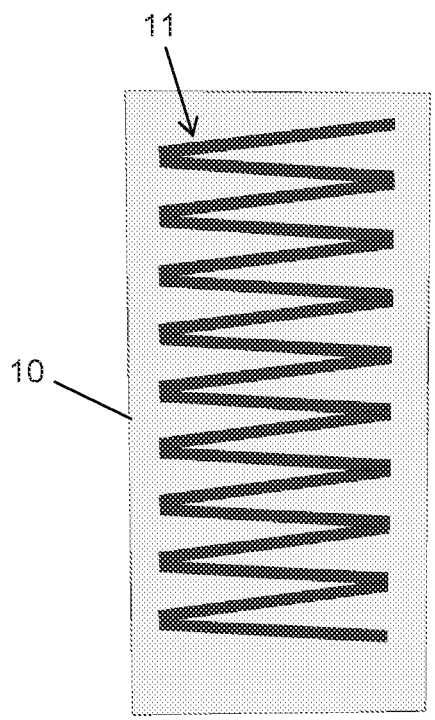
FIG. 3 schematically illustrates an exemplary electro-active polymer, printed or etched with a conductor in a zigzag pattern in an expanded state, according to some embodiments of the present invention.

FIG. 2 shows an exemplary electro-active polymer that can be used in accordance with some embodiments of the present invention. As FIG. 2 shows, the electro-active polymer can be used as a linear actuator. The electro-active polymer, generally indicated by numeral 10 in the FIG. 2, includes at least: a layer of semi-stiff conductor 11 printed on both sides of its surfaces. In some embodiments, the semi-stiff conductor layer 11 is printed or etched in a zigzag form, such that the deployment form of the semi-stiff conductor 11 keeps the electro-active polymer in a pre-stretched state while allowing it to expand in a linear direction. FIG. 3 schematically illustrates the exemplary electro-active polymer 10 in an expanded state.

Figure 4:
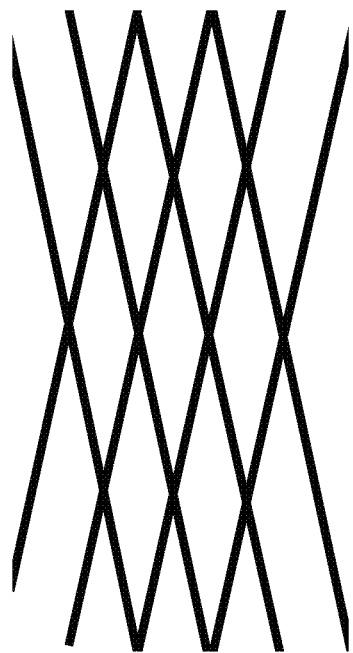
FIG. 4 schematically illustrates an example of an expanding pattern, according to some embodiments of the present invention.

Although the maintaining/strengthening/expanding pattern of the semi-stiff conductor 11 is shown with respect to the zigzag form, other forms of maintaining patterns can also be used, such as a expanding diamond pattern. FIG. 4 schematically illustrates an example of a lattice work form, according to some embodiments of the present invention.

In some embodiments, as illustrated in at least some figures, the arrangement of the exemplary electro-active polymer with the exemplary conductor results in a flat and flexible linear actuator which can fold.

Figures 5A, 5B:
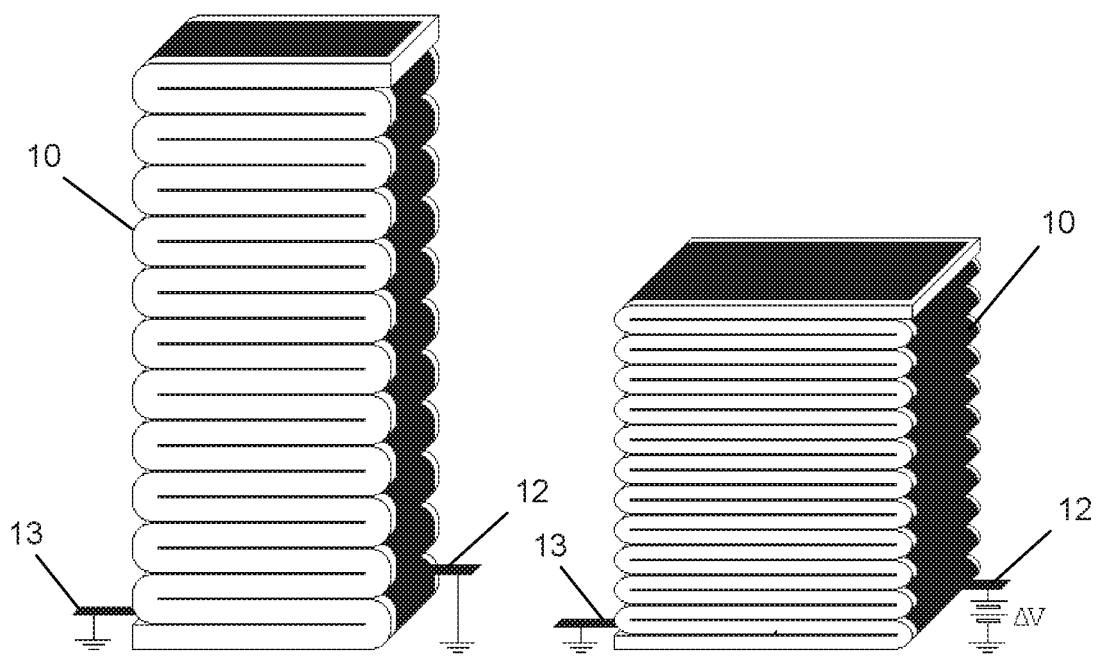
FIGS. 5A and 5B are perspective views, showing an exemplary electro-active polymer actuator folded, according to some embodiments of the present invention.

FIG. 5A is a perspective view, showing an exemplary pre-stretched electro-active polymer 10 folded in order to improve capabilities of the actuator, according to some embodiments of the invention. FIG. 5A shows the exemplary electro-active polymer 10 to be folded in an alternating folding pattern. FIG. 5B is a perspective view, showing the linear expansion of the exemplary folded electro-active polymer 10, having a pair of mechanical connectors (12 and 13) at each end of an active region of the electro-active polymer 10.

Figure 6A:
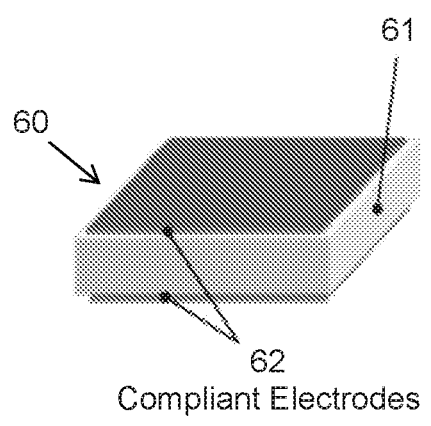
FIGS. 6A and 6B schematically illustrate a top perspective view of an exemplary electro-active polymer transducer before and after application of a voltage in accordance with some embodiments of the present invention.
Figure 6B:
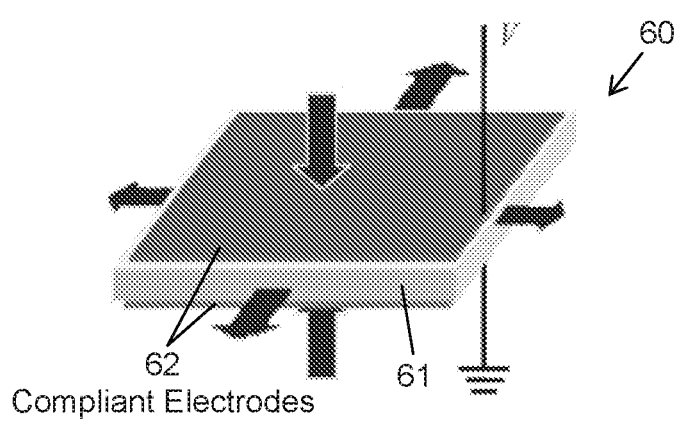

FIGS. 6A and 6B schematically illustrate a top perspective view of an exemplary electro-active polymer transducer 60 before (FIG. 6A) and after (FIG. 6B) application of a voltage, in accordance with some embodiments of the present invention. In some embodiments, the transducer (60) includes an exemplary EAP (61) with a conductive coating that is activated by electrostatic forces between two compliant electrodes (62), which are fundamentally capacitors that change their capacitance when a voltage is applied by allowing the polymer to compress in thickness and expand in area due to the electric field (the expansion is indicated by the black arrows in FIG. 6B).

Figure 7A:
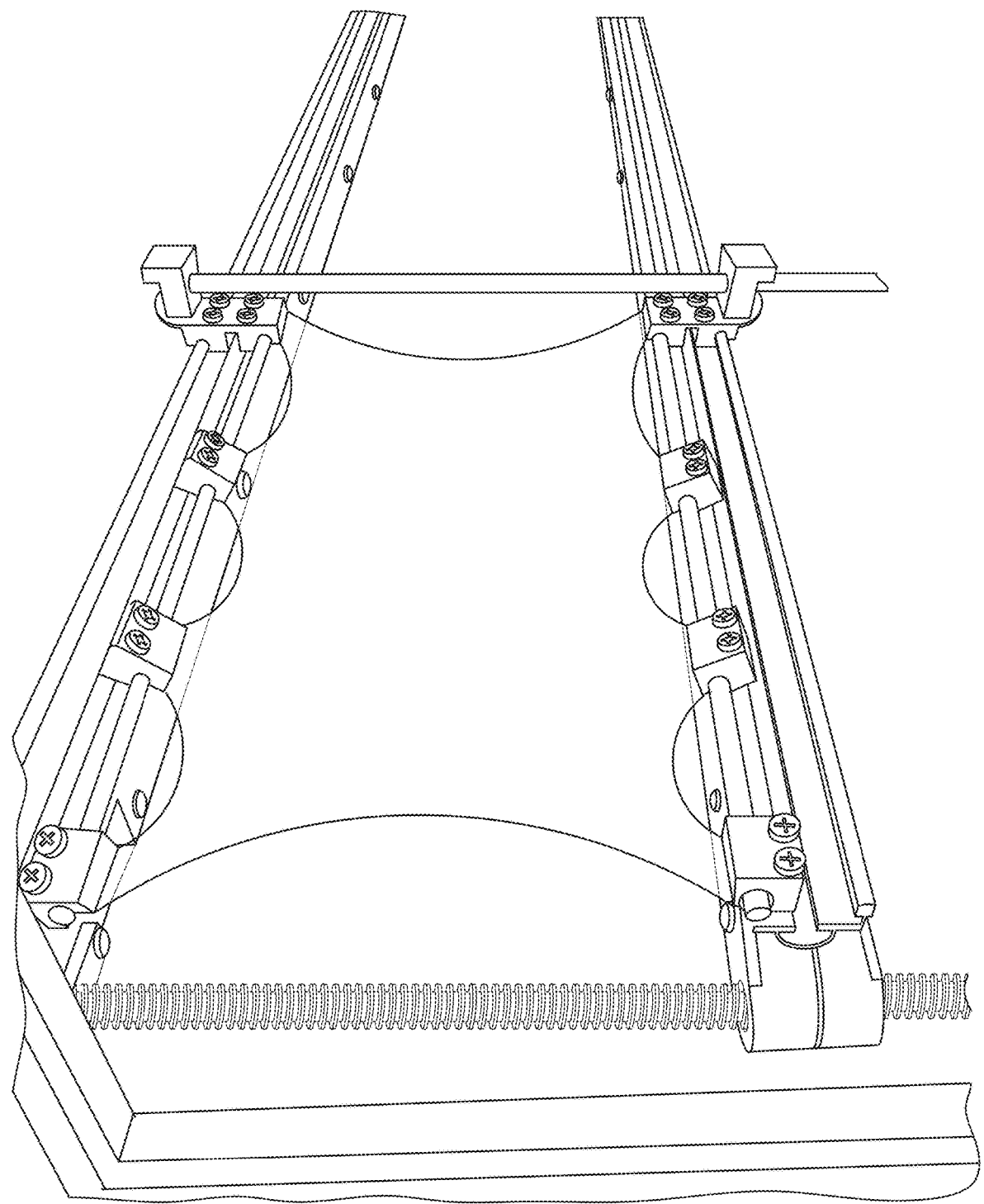
FIGS. 7A-7C are snapshots of an example of a stretching device intended to biaxially or single axially pre-stretch an electro-active polymer film, in the fabrication process, according to some embodiments of the present invention.
Figure 7B:
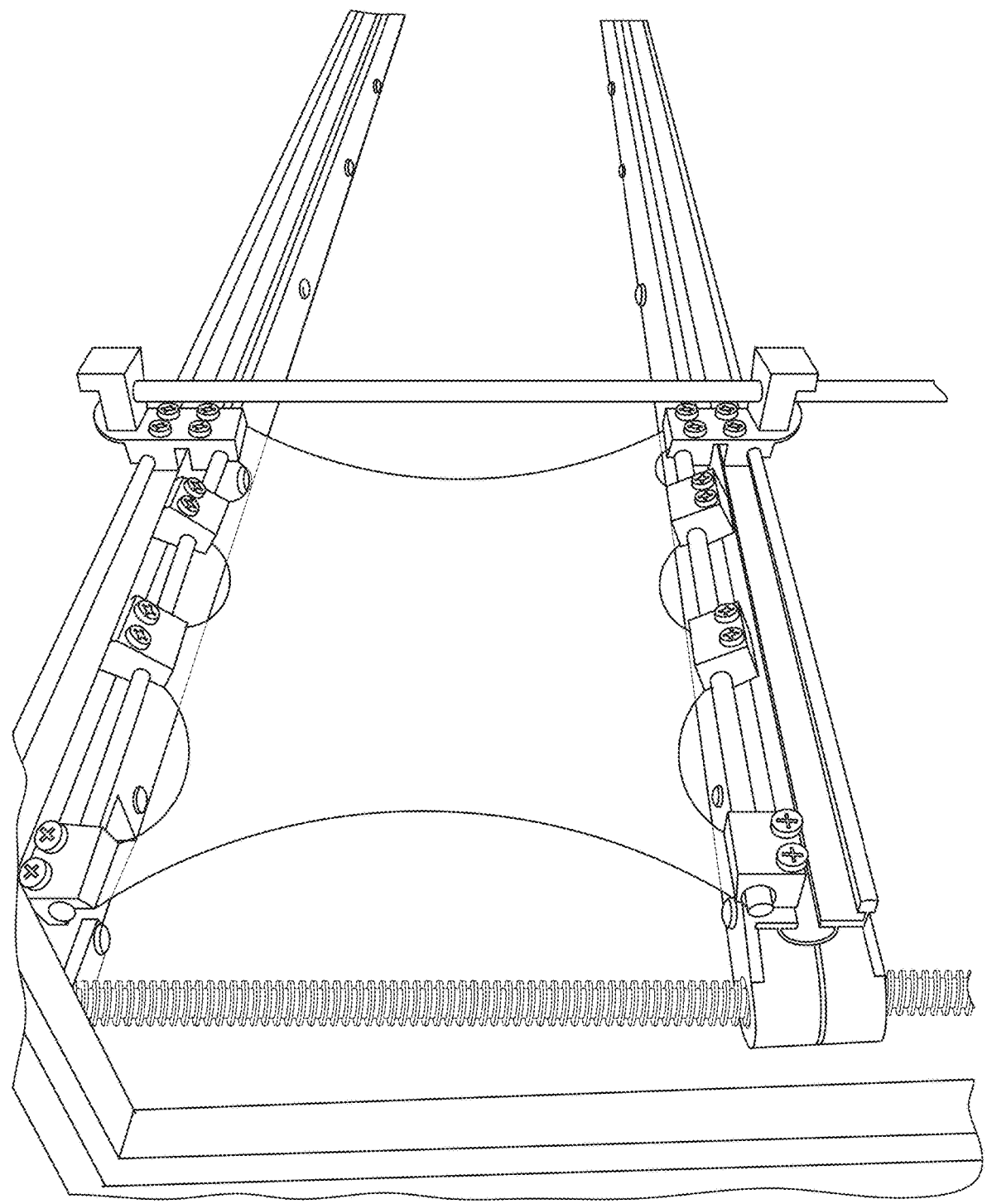
Figure 7C:
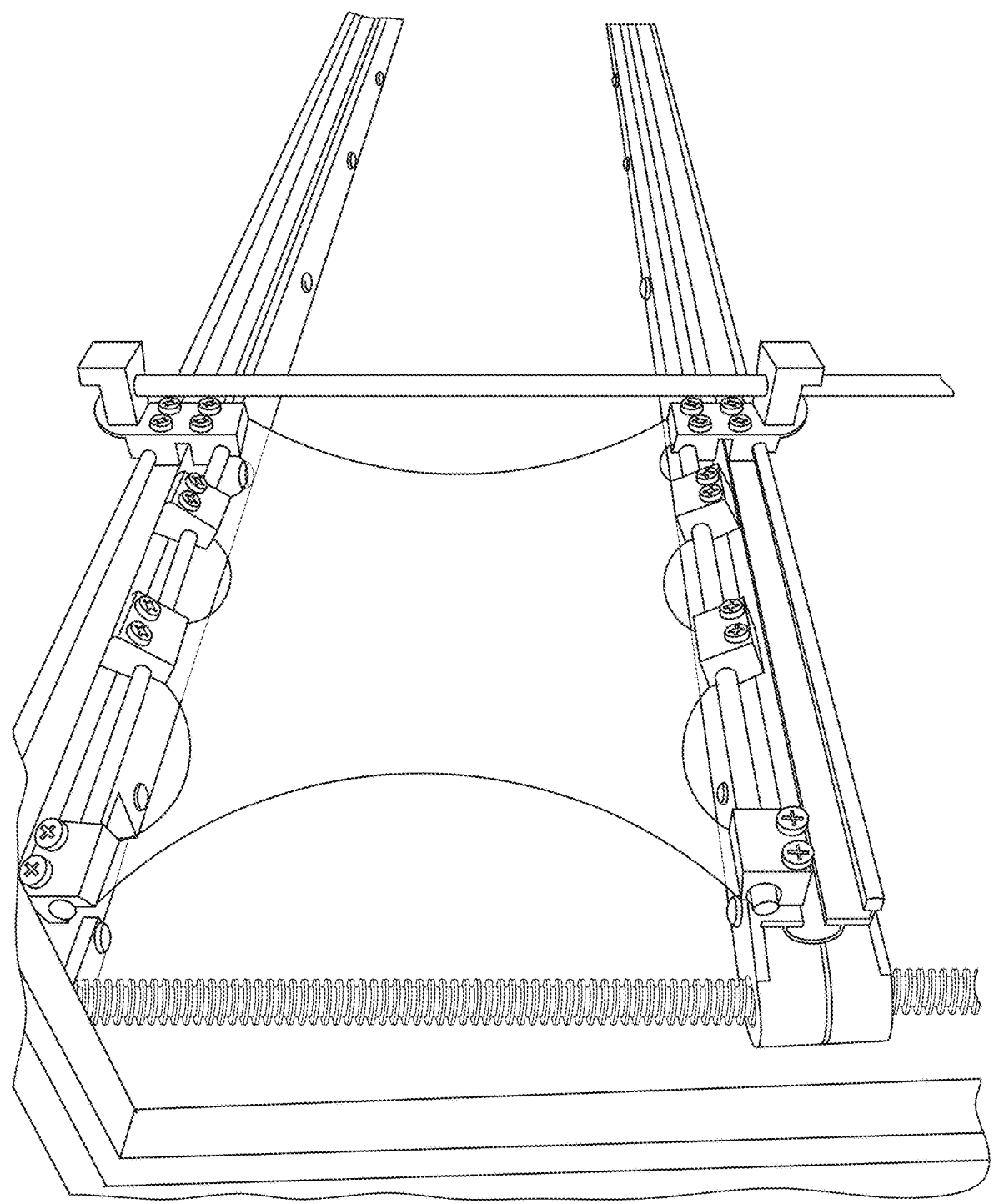

FIGS. 7A-7C shows an example of a stretching device intended to biaxially or single axially pre-stretch a transparent electro-active polymer film. The EAP film is fixed by 8 connectors to the stretching device, which expands the film in the desired directions (e.g., biaxial). The stretching device can be used in step 1 of FIG. 1 for mechanically biaxially pre-stretching an electro-active polymer film in the exemplary procedure for maintaining an electro-active polymer in the pre-stretch state/condition. FIG. 7A shows a biaxially stretched EAP film, which is further stretched in FIGS. 7B and 7C, until the film reaches its desired pre-stretched state of 500% of its original size on FIG. 7C.

The term semi-stiff conductor is being used to describe a stretchable conductor or a rigid conductor in an expanding pattern that once attached to the EAP is rigid enough to hold the EAP in a pre-stretched state, while allowing the EAP to expand. For example, on a 1×1 cm2 3M 4905 VHB tape, equally biaxially pre-stretched 5 times of the film's original size, meaning that the 1×1 cm2 film was stretched by $\sqrt{5}$ times of the film's original size in length (X axis) and in width (Y axis). The conductor won't compress by more than 10%, due to a mechanical compression force of at least 500N on the X axis and on the Y axis, on a 1×1 cm2 surface. Meanwhile, the conductor allows the EAP film to mechanically expand by at least 7% on a single or both axis, while maintaining at least 5% of its conductivity for every 7% of expansion.

The precise compression force the conductor will be able to resist, and the expansion the conductor can perform while maintaining conductivity, is determined by the material the conductor is made of, the shape, size and pattern of the conductor and the method of attaching the conductor to the EAP.

Figure 8:
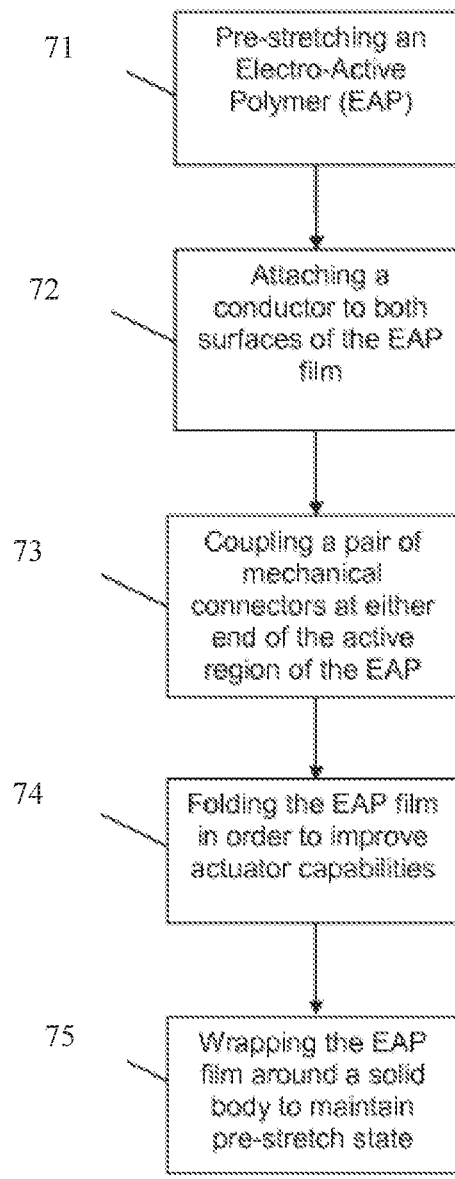
FIG. 8 is a flow chart generally illustrating an exemplary procedure for maintaining an electro-active polymer in a pre-stretch state, according to some embodiments of the present invention.

Exemplary Methods and Mechanisms for Maintaining an Electro-Active Polymer Film in a Pre-Stretch State by Wrapping it Around a Solid Body FIG. 8 is a flow chart generally illustrating an exemplary procedure for maintaining an electro-active polymer in the pre-stretch state/condition, according to some embodiments of the present invention. In some embodiments, this procedure can include at least the steps of:

mechanically biaxially pre-stretching an electro-active polymer film (step 71);

attaching at least one semi-stiff or stretchable conductor to the pre-stretched electro-active polymer with one of the following ways, but not limited to: printing (e.g., conducting ink), etching (e.g. by using a solution of electrolyte), brushing (e.g. using carbon graphite powder with silicon oil), water dispersion (e.g. using PAni based solution), gluing (e.g. gluing a laser cut or molded into an expanding pattern such as zigzag or expanding diamond pattern, rigid conducting sheet), or any other suitable attachment method(s) (step 72);

coupling a pair of mechanical connectors at either end of the active region of the electro-active polymer (step 73);

folding the electro-active polymer film in order to improve capabilities of an actuator (i.e., the electro-active polymer with the attached conductor) (step 74); and wrapping the electro-active polymer film around a solid body and fixing/maintaining (e.g., securing, attaching) it in that state, to keep the film in a pre-stretched state (step 75).

Figure 10:
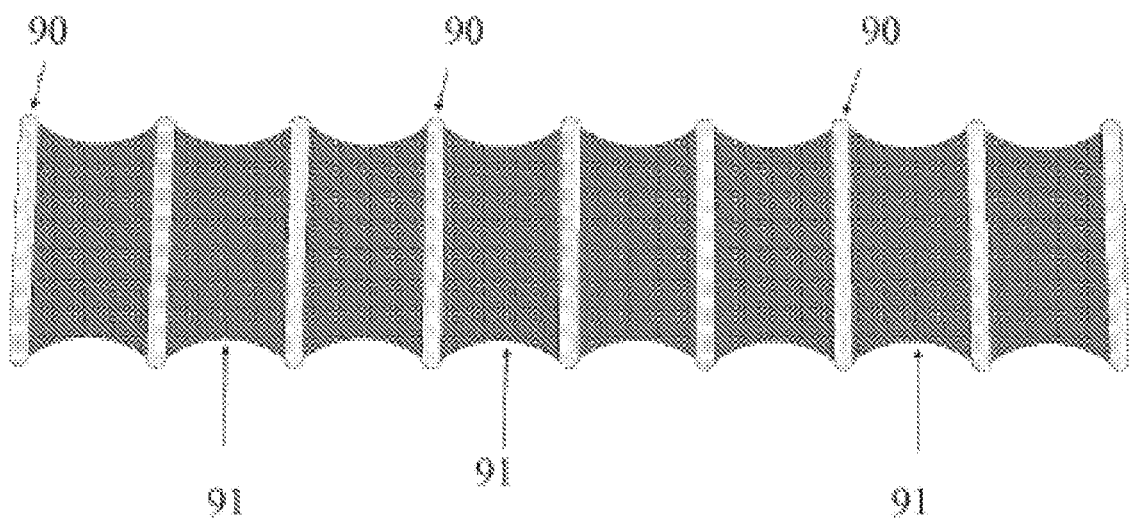
FIG. 10 is a snapshot that schematically illustrates an example of a solid mechanism for fixing the EAP film in a pre-stretch state in a single axis, while allowing the film to expand in the other axis, according to some embodiments of the present invention.

FIG. 10 schematically illustrates an example of a solid mechanism for fixing the EAP film in a pre-stretch state in a single axis, while allowing the film to expand in the other axis.

In some embodiments, the electro-active polymer film might be fixed in a pre-stretched state on a single axis, by a solid mechanism, for example but not limited to, parallel solid plastic straps attached to the EAP film (such as in FIG. 10), allowing the EAP film to expand and be wrapped around a solid body on the other axis. In some embodiments, the attachment of the solid mechanism can be made, for example but not limited to, gluing and/or any other similarly method(s) of attachment. FIG. 10 shows an example in which parallel solid plastic straps (90) are attached to an EAP film (91) thus maintaining the film pre-stretch on a single axis (in the direction of the plastic straps), but also allowing the EAP film to expand in the other axis. In some embodiment, the solid plastic straps might be 1 mm-80 cm wide. In some embodiment, the solid plastic straps might be 1 mm-20 cm wide. In some embodiment, the solid plastic straps might be 1 cm-80 cm wide. In some embodiment, the solid plastic straps might be 1 cm-20 cm wide. In some embodiment, the solid plastic straps might be 1 cm-60 cm wide. In some embodiment, the solid plastic straps might be placed in distance of 1 mm-50 cm apart. In some embodiment, the solid plastic straps might be placed in distance of 1 cm-50 cm apart. In some embodiment, the solid plastic straps might be placed in distance of 1 cm-30 cm apart. In some embodiment, the solid plastic straps might be placed in distance of 1 cm-20 cm apart. In some embodiment, the solid plastic strap might be placed in parallel or any angle between 180° to 90° from each other. In some embodiment, the plastic straps can be made from polypropylene, polystyrene, polyethylene, nylon, rubber or any other similar type plastic.

In some embodiments, the plastic straps used to fix the pre-stretched film in a single axis, can also be used to prevent the film from contracting in the other axis, by attaching holders that keep the plastic straps at a minimal distance, while allowing them to expand. In some embodiments, the holder can be made by using an elastic wire, with a rigid cover, in the space between the plastic straps (such as in FIGS. 13A-13B)

In some embodiments, the precise pre-stretch of the electro-active polymer film, can be determined by visual indicator, e.g. a hills and valleys pattern with a solid strap (such as in FIG. 9A-9C) or by pre-arranged guide lines or any other kind of visual indicator.

Figure 9A:
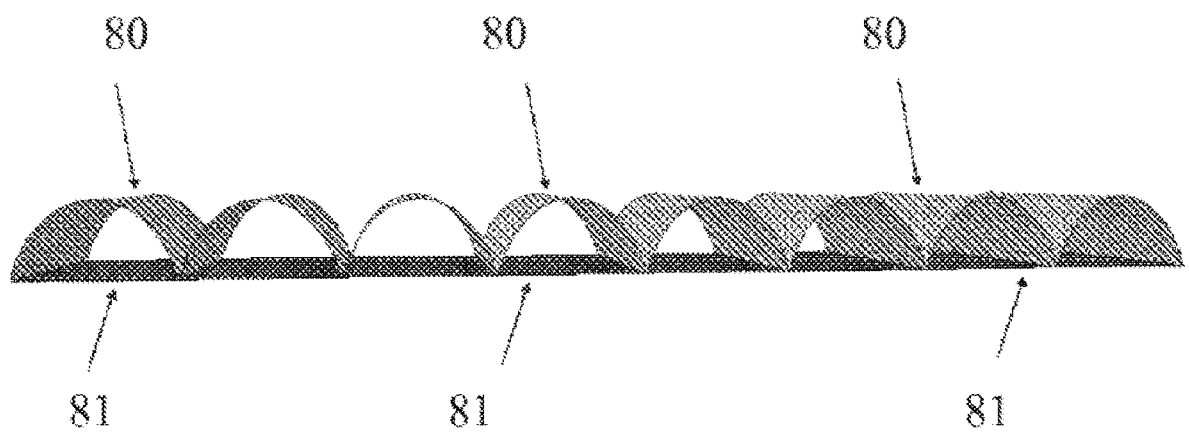
FIGS. 9A-9C schematically illustrate a hills and valley pattern that can be used as a visual indicator for wrapping the EAP film with the precise amount of stretch, according to some embodiments of the present invention.
Figure 9B:
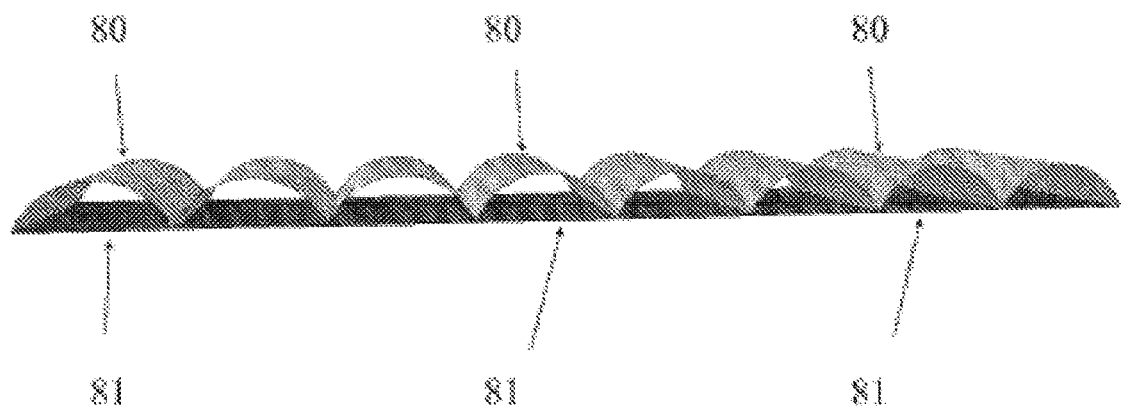
Figure 9C:
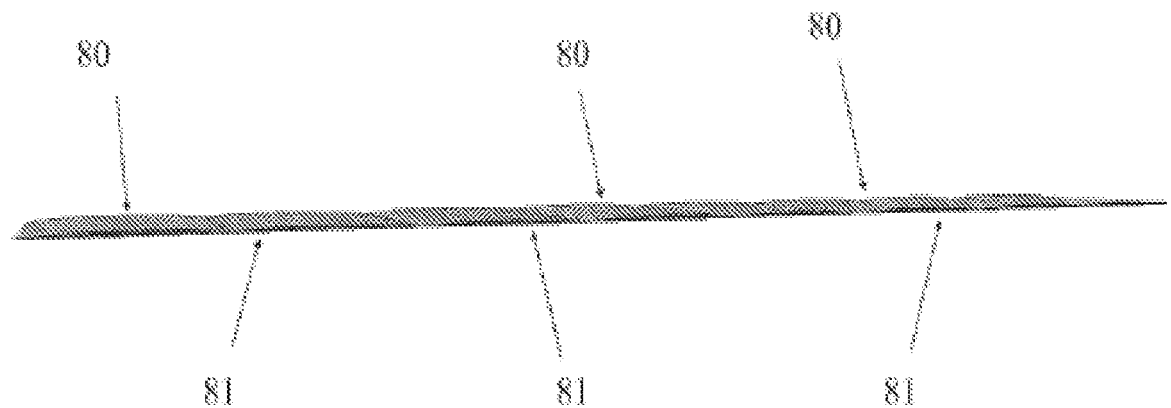

FIGS. 9A-9C schematically illustrate a hills and valley pattern that can be used as a visual indicator for wrapping the EAP film with the precise amount of stretch. FIG. 9A shows an EAP film (81) attached to a strap (80) (for example polypropylene, flat nylon, polyester, seatbelt strap or any other strap), on multiple joints, when the strap's length is longer than the EAP film's length, causing a hills and valleys pattern on the strap. FIG. 9B shows that the EAP film (81), can be linearly stretched while the strap (80) remains loose. FIG. 9C shows that the strap limits the linear stretch of the EAP film, due to the strap firmness, thus preventing tear in the EAP film, and giving a visual indicator for when the EAP film is precisely pre-stretched, which happens when the strap and the EAP film are in the same length.

In some embodiments, the present invention is directed to a method for maintain an electro-active polymer film in a pre-stretched state, where the method at least includes the steps of:

pre-stretching the electro-active polymer film, by mechanically stretching the film in a single or biaxial directions;

fixing the EAP film in a pre-stretch state on a single axis, by attaching straps that allow the EAP film to expand in the other axis, by, for example but not limited to, gluing and/or any other similarly method(s) of attachment;

attaching at least one conductor to at least one surface of the electro-active polymer film, by, for example but not limited to, printing, etching, brushing, water dispersion, gluing and/or any other similarly suitable method(s) of attachment;

at least one of said conductor, features the capability of maintaining conductivity at a level of at least 5% while being stretched for more than 5%;

wrapping and fixing the electro active polymer film around solid body, for example but not limited to a human body part; and fixation can be made by Velcro, clip-on button, buttons, zipper or any other similar fixation method.

Exemplary Embodiments of Electro-Active Polymer Based Compression Bandage Made in Accordance with the Present Invention.

In some embodiments, the EAP actuator can be used for the construction of an active compression bandage, including of: a bandage, which is placed on a body part, for example, but not limited to, a leg, a calf, a foot, a hand or an arm; for example, the bandage is fixed on the body part, by using, for example, between 1 to 20 elastic straps (can be in another similarly suitable attaching mechanism), which are, for example, wrapped around the body part, and are connected to the bandage by Velcro, clip-on buttons, buttons, zipper, sewing or any other similar fixation device and method. In some embodiments, the elastic straps are stretched when wrapped around the body part. In some embodiments, the bandage and the elastic straps are threaded with EAP actuators. In some embodiments, by stretching the elastic straps, the EAP actuators are pre-stretched, and, then, are fixed in a pre-stretch state.

In some embodiments, the bandage is connected to a control box, which activates and controls the EAP actuators activation. In some embodiments, the control box at least includes: a battery and an electrical circuit, which transforms the battery output voltage to the required voltage for the EAP and activates and de-activates the EAP actuators, by applying voltage on each actuator, separately or simultaneously, according to a pre-determined sequence.

In some embodiments, the control box can include a feedback mechanism configured to measure the pressure applied by the EAP actuator, and/or configured to adjust the voltage applied on the EAP actuator so as to result in achieving the required pressure. In some embodiments, the measuring of the pressure can be made by a pressure sensor.

In some embodiments, the control box can include a feedback mechanism configured to monitor heart rate and/or a blood flow, so as to synchronize the EAP actuators activation timing accordingly.

In some embodiments, the electrical charge being applied on the EAP is between 10-20,000 volts. In some embodiments, the electrical charge being applied on the EAP is between 100-20,000 volts. In some embodiments, the electrical charge being applied on the EAP is between 1,000-20,000 volts. In some embodiments, the electrical charge being applied on the EAP is between 10-1,000 volts. In some embodiments, the electrical charge being applied on the EAP is between 10-10,000 volts. In some embodiments, the electrical charge being applied on the EAP is between 10,000-20,000 volts.

In some embodiments, the bandage is fixed on the body part by using between 1-15 straps. In some embodiments, the bandage is fixed on the body part by using between 1-10 straps. In some embodiments, the bandage is fixed on the body part by using between 1-5 straps. In some embodiments, the bandage is fixed on the body part by using between 5-20 straps. In some embodiments, the bandage is fixed on the body part by using between 10-20 straps. In some embodiments, the bandage is fixed on the body part by using between 15-20 straps.

In some embodiments, the required stretch of the strap can be determined by a visual indicator, e.g. a hills and valley pattern with a solid strap or by pre-arranged guide lines or any other kind of visual indicator.

In some embodiments, activating the EAP actuator provides pressure of between 10 mmHg and 200 mmHg on the body part.

In some embodiments, the activation of the EAP actuators can be made to apply static compression, sequential compression, segmental compression, intermittent compression, or any other type of compression. In some embodiments, the active compression bandage can be used for the prevention and/or treatment for various vascular or lymphatic diseases, for example, but not limited to, DVT (Deep Vein Thrombosis), lymphedema, varicose veins, spider veins, CVI (Chronic Venous Insufficiency), ulcers, superficial venous thrombosis or phlebitis and diabetic wounds. In some embodiments, the active compression bandage can be used for the prevention and/or treatment and/or reduction of, for example, but not limited to, scar tissue, swelling, sore muscles, migraines, burn wounds, cellulitis, chronic edema, eczema, infected wounds and epidermolysis bullosa. In some embodiments, the active compression bandage can be used to reduce the recovery time of orthopedic surgeries, swelling, infections and sport injuries. In some embodiments, the active compression bandage can be used to assist in rehabilitation of mobility and physiotherapy.

In some embodiments, the active compression bandage might include feedback mechanism, which measures the pressure applied by the EAP actuator. In some embodiments, the feedback mechanism can be made by a pressure sensor. In some embodiments, the active compression bandage might include a heart rate monitor or a blood flow monitor. In some embodiments, said monitor is used to synchronize the timing of the activation of the EAP actuators.

In some embodiments, the active compression bandage is controlled by a control unit. In some embodiments, the control unit might be battery operated. In some embodiments, the control signal from said control unit is a voltage. In some embodiments, the control unit controls the applied pressure and the timing of the EAP actuators.

In some embodiments, the active compression bandage can be formed as a stocking or legging to be put on the leg.

In some embodiments, wrapping the elastic strap will stretch the EAP strap by between 20% and 1000%. In some embodiments, wrapping the elastic strap will stretch the EAP strap by between 20% and 500%. In some embodiments, wrapping the elastic strap will stretch the EAP strap by between 50% and 1000%. In some embodiments, wrapping the elastic strap will stretch the EAP strap by between 100% and 1000%. In some embodiments, wrapping the elastic strap will stretch the EAP strap by between 100% and 500%. In some embodiments, wrapping the elastic strap will stretch the EAP strap by between 50% and 800%.

In some embodiments, the active compression bandage can be formed as a stocking to be put on the leg. In some embodiments, the active compression bandage can be formed to use on various body parts, for example, the leg, the calf, the hip, the hand, the arm, the shoulder, the foot or any other body part.

The term "activating the EAP actuator" is used to describe a process of discharging the electric charge from the EAP actuator by at least 8%, causing the EAP actuator to contract by at least 1%. The exact amount of contraction, will be determined by the amount of pre-stretch, the type of conductor used, the method of attachment for said conductor, the number of layers of EAP film the EAP actuator is comprised from and the amount of the electric charge being released.

The term "active compression bandage" refers to a device, which applies different compression on a body part. The pressure is higher when the bandage's actuator is activated (e.g., but not limited to, between 10 mmHg and 200 mmHG), and lower when the bandage's actuator is de-activated/not active (e.g., but not limited to, between 0 mmHg and 80 mmHg).

In some embodiments, while the EAP actuator is not active, the active compression bandage applies pressure of between 0 mmHg and 80 mmHg. In some embodiments, while the EAP actuator is not active, the active compression bandage applies pressure of between 5 mmHg and 80 mmHg. In some embodiments, while the EAP actuator is not active, the active compression bandage applies pressure of between 0 mmHg and 30 mmHg. In some embodiments, while the EAP actuator is not active, the active compression bandage applies pressure of between 5 mmHg and 40 mmHg.

In some embodiments, activating the EAP actuator provides pressure of between 10 mmHg and 200 mmHg on the body part. In some embodiments, activating the EAP actuator provides pressure of between 10 mmHg and 100 mmHg on the body part. In some embodiments, activating the EAP actuator provides pressure of between 20 mmHg and 200 mmHg on the body part. In some embodiments, activating the EAP actuator provides pressure of between 20 mmHg and 100 mmHg on the body part. In some embodiments, activating EAP actuator provides pressure of between 30 mmHg and 130 mmHg on the body part.

In some embodiment, the electro-active polymer actuator, can be used to create an electrical tourniquet, used to control venous and arterial circulation to an extremity for a period of time, according to an electrical signal.

In some embodiment, the electro-active polymer actuator, can be used to create a cuff for a blood pressure monitor, used to measure blood pressure.

In some embodiment, the electro-active polymer actuator, can be used to create a haptic feedback device, which recreates a sense of touch, by applying forces, vibrations or motions to the user.

In some embodiment, the electro-active polymer actuator, can be used to create a robotic prosthesis, and mimic the actions of a muscle in producing force and movement.

In some embodiment, the electro-active polymer actuator, can be used to create a general purpose linear actuator that creates motion in a straight line, for various applications such as industrial machinery, computers, valves or any other application which requires linear motion.

In some embodiment, the electro-active polymer actuator, can be used to create a general purpose circular actuator that creates motion in a radial direction, for various applications such as industrial machinery, pumps, valves or any other application which requires radial motion.

In some embodiment, the electro-active polymer actuator, can be used to create a self-stabilizing or self-leveling platform, robot, machine, orthopedic shoe, or any other type device.

In some embodiment, the electro-active polymer actuator, can be used to create a mobility aid or bionic walking assistance device, that uses powered leg or arm attachments to enable movement or rehabilitation of the arms or legs for paraplegics, tetraplegics, or any other type of paralysis, partial paralysis or weakness of a limb.

In some embodiment, the electro-active polymer actuator, can be used to create a shock absorber, designed to absorb and damp shock impulses.

In some embodiment, the electro-active polymer actuator, can be used to create a pump that moves fluids (liquids or gases), or sometimes slurries, by mechanical action.

Figure 11A:
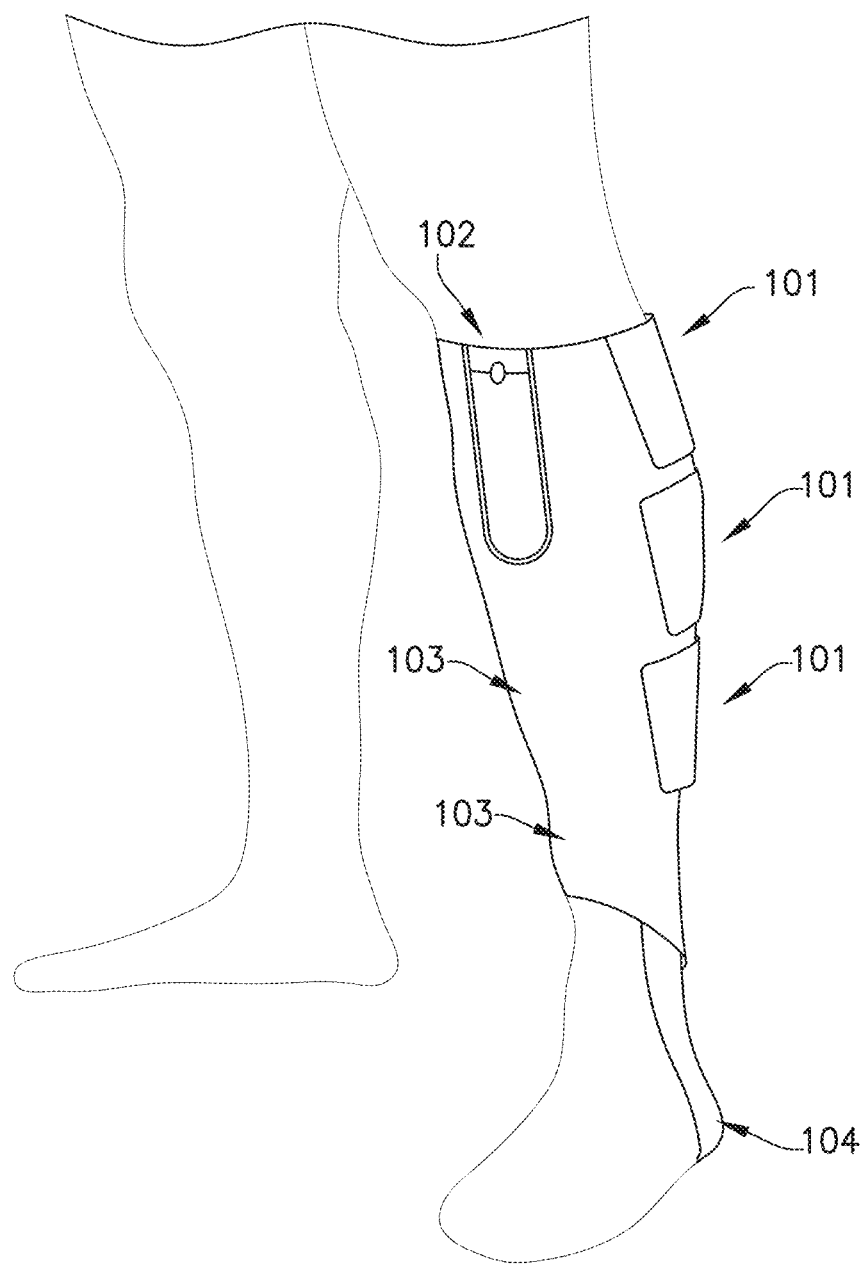
FIGS. 11A-11C are snapshots that schematically illustrate examples of an external design of an active compression bandage for the leg, according to some embodiments of the present invention.
Figure 11B:
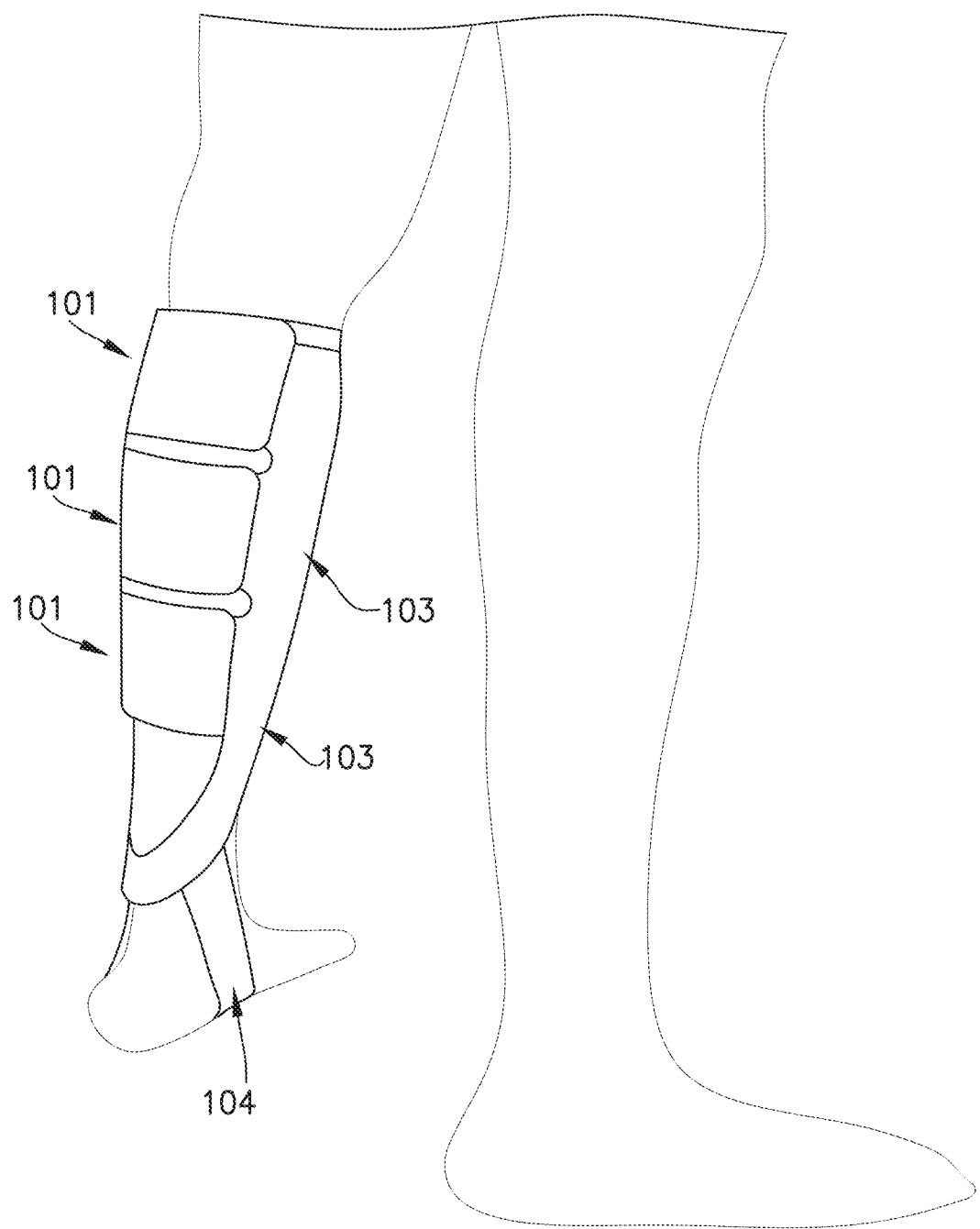
Figure 11C:
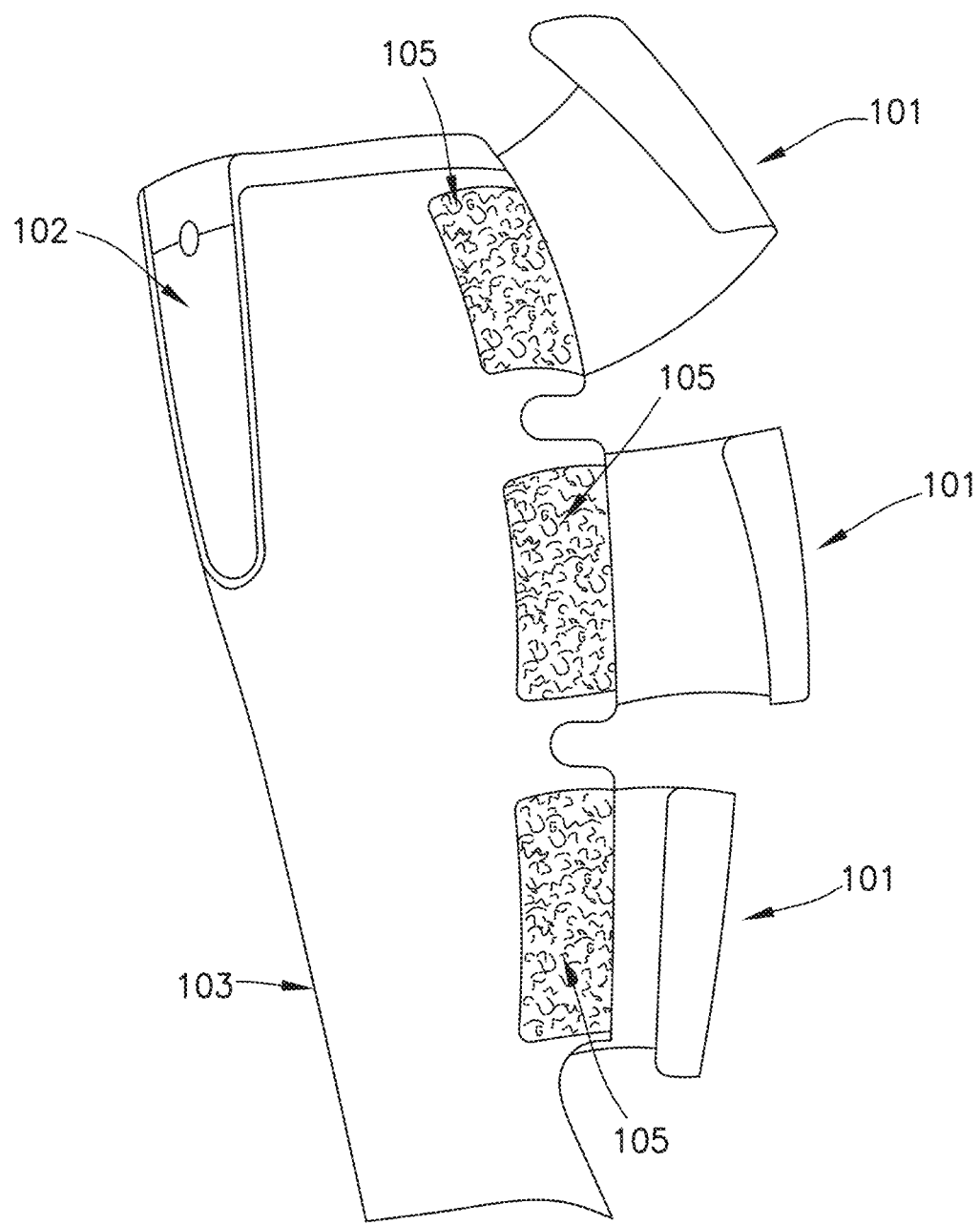

FIGS. 11A-11C schematically illustrate an example for an external design of an active compression bandage for the leg. FIG. 11A show a front view of the active compression bandage on a leg. Three elastic straps (101) are wrapped and stretched around the leg, and are fixed to the bandage (103) by Velcro. The active compression bandage is controlled by a control box (102). An additional strap (104) is used to indicate the correct location for the placement of the active compression bandage on the leg. FIG. 11B show a rear view of the active compression bandage on a leg. FIG. 11C shows a side view of the active compression bandage, unworn, showing the Velcro connectors (105).

Figure 12A:
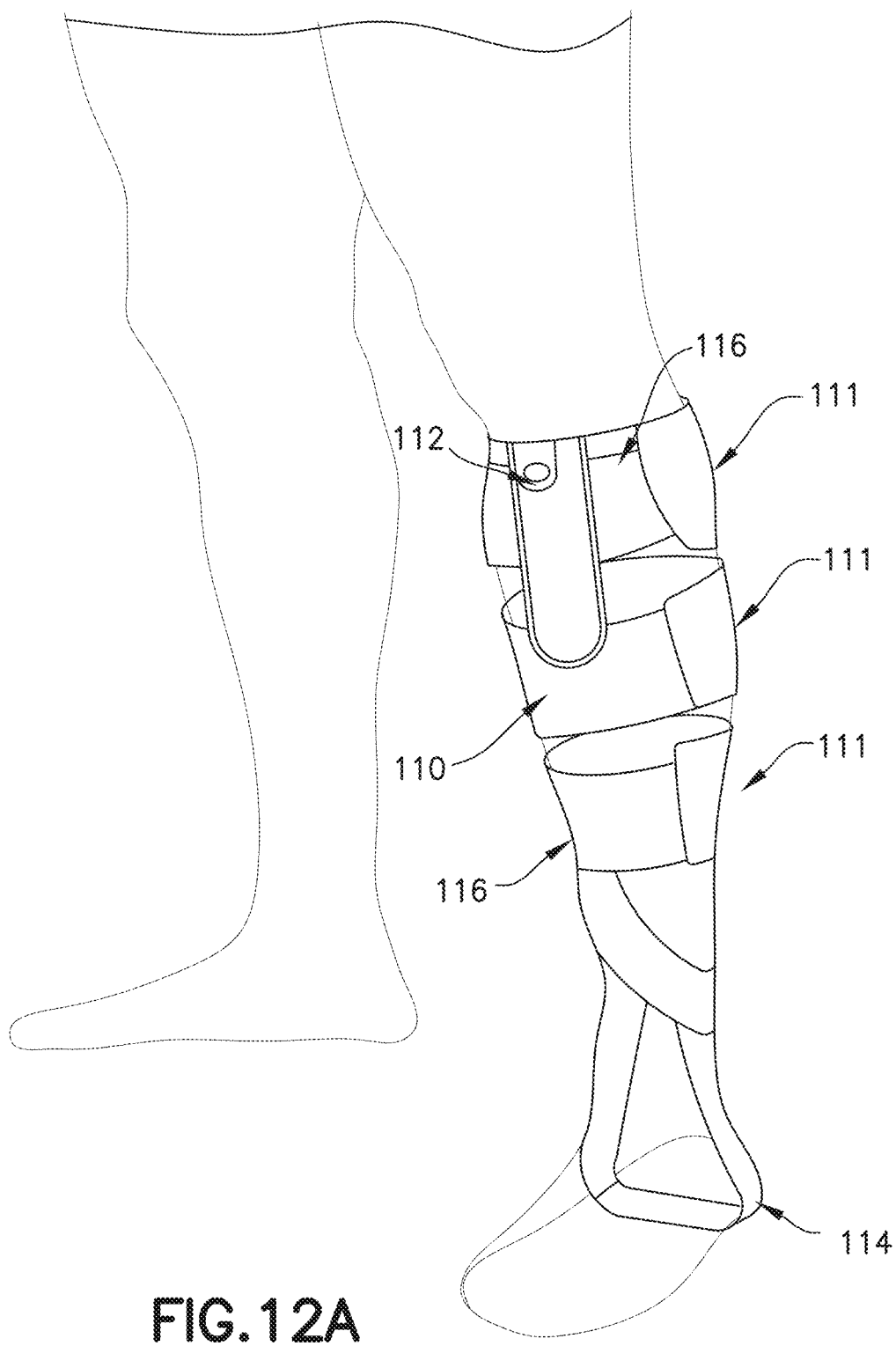
FIGS. 12A-12B are snapshots that schematically illustrate example(s) of an internal mechanism that activates an active compression bandage for the leg, built from EAP actuators, according to some embodiments of the present invention.
Figure 12B:
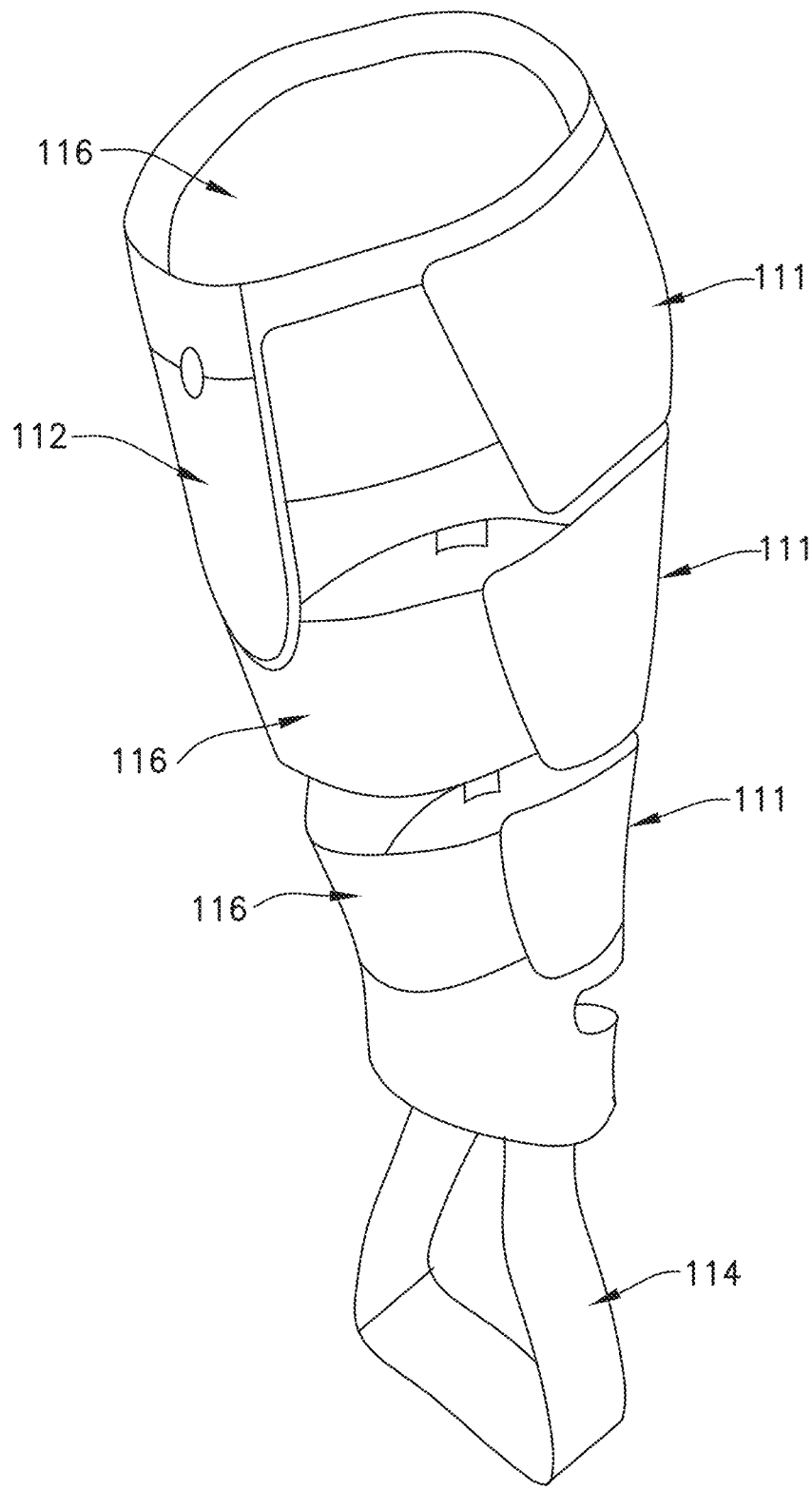

FIGS. 12A-12B schematically illustrate an example for an internal mechanism that activates a compression bandage for the leg, built from EAP actuators. FIG. 12A shows a front view of the internal construction of the active compression bandage on a leg. Three elastic straps (111) are wrapped and stretched around the leg, pre-stretching the EAP actuator (116) and fixing it around the leg. The active compression bandage is controlled by a control box (112). An additional strap (114) is used to indicate the correct location for the placement of the active compression bandage on the leg. FIG. 12C shows a side view of the internal construction of the active compression bandage, worn but without the leg, showing that the EAP actuator (116) is fully wrapped around the leg, giving a full peripheral compression when activated.

Figure 13A:
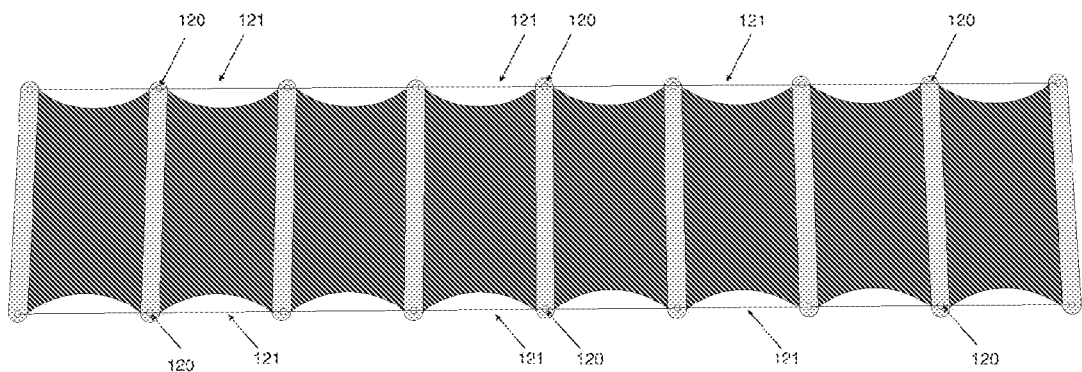
FIGS. 13A-13B are snapshots that schematically illustrate an example of an addition to the solid mechanism for fixing the EAP film in a pre-stretch state in a single axis, which prevents the film from contracting in the other axis, according to some embodiments of the present invention.
Figure 13B:
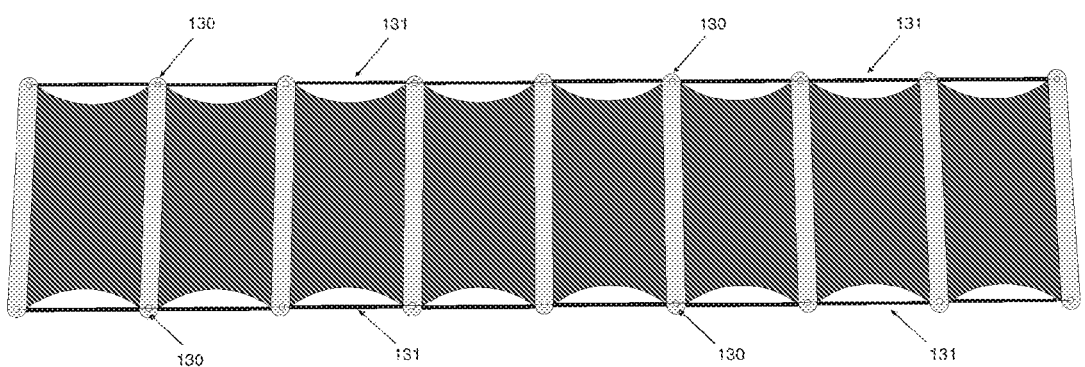
Figure 14A:
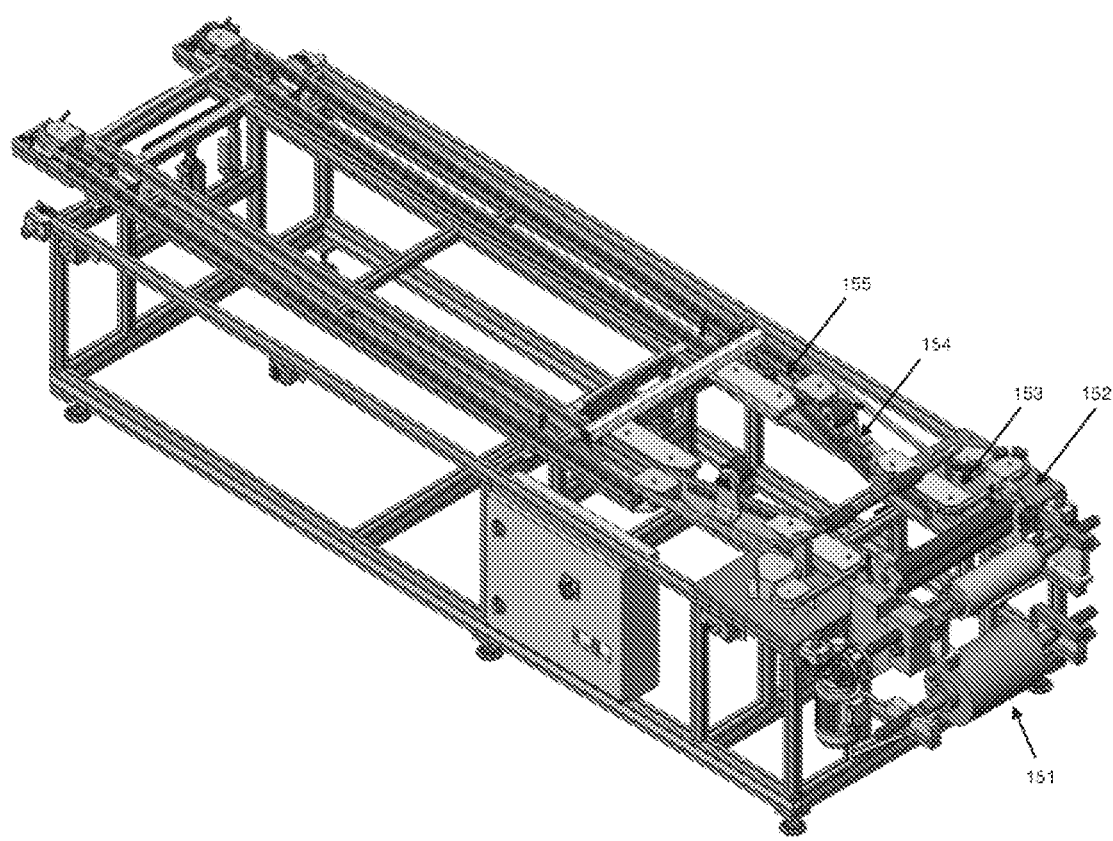
FIGS. 14A-14D are snapshots that schematically illustrate of an example of a stretching machine intended to biaxially or single axially pre-stretch an electro-active polymer film, in the fabrication process, according to some embodiments of the present invention.
Figure 14B:
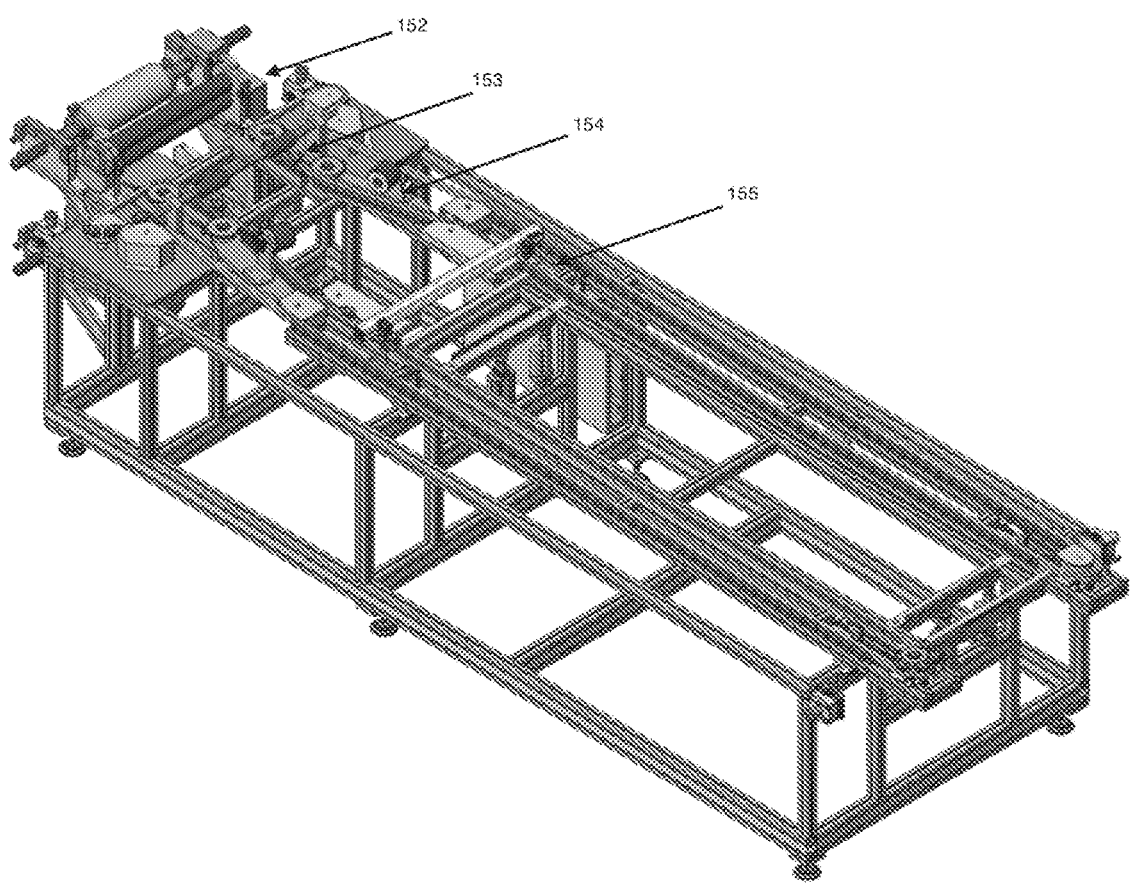
Figure 14C:
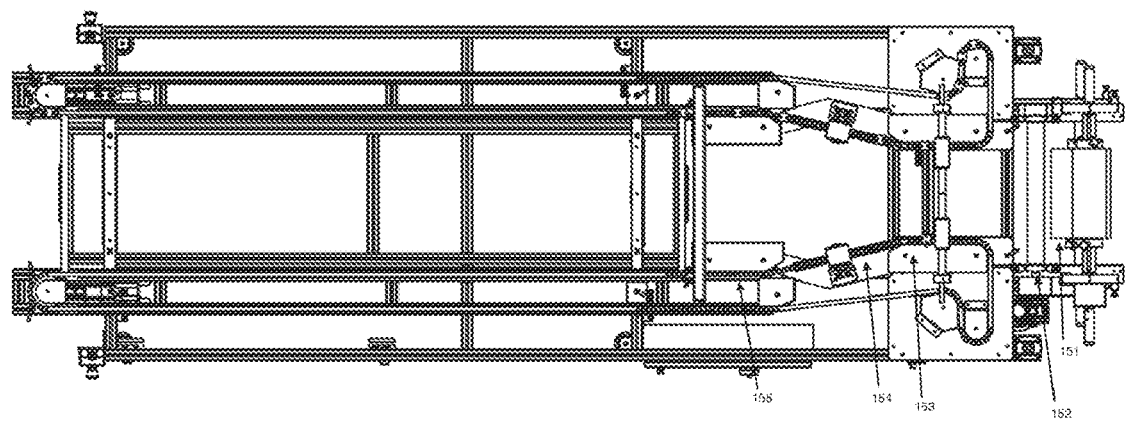
Figure 14D:
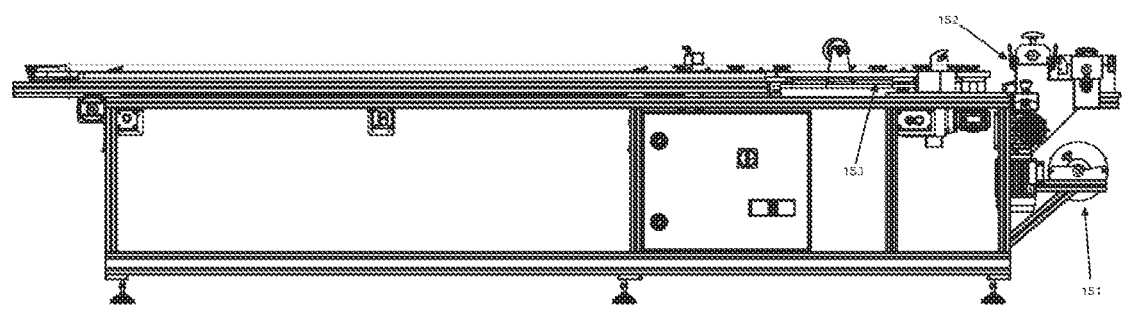

FIGS. 13A-13B schematically illustrate an example of an addition to the solid mechanism for fixing the EAP film in a pre-stretch state in a single axis, by using an elastic wire (121) which is threaded through holes in the plastic holders (120 & 130). The wire has a rigid cover (131) in space between the holders, which prevents the film from contracting in the other axis, while allowing it to expand.

FIGS. 14A-14D show an example of a stretching machine intended to biaxially or single axially pre-stretch an electro-active polymer film. A roll of EAP film tape is held on a bar (151). Two rolling bars (152) pull the EAP film from the roll, and separate it from its protecting liner. The film is later attached to a moving rail (153). The speed difference between the two rolling bars (152) and the moving rail (153), stretches the EAP film in the axis of the moving rail. The moving rail later expands (154) until it gets to its final width (155). The rails expansion, stretches the EAP film perpendicularly to the axis of the moving rail.

Figure 15:
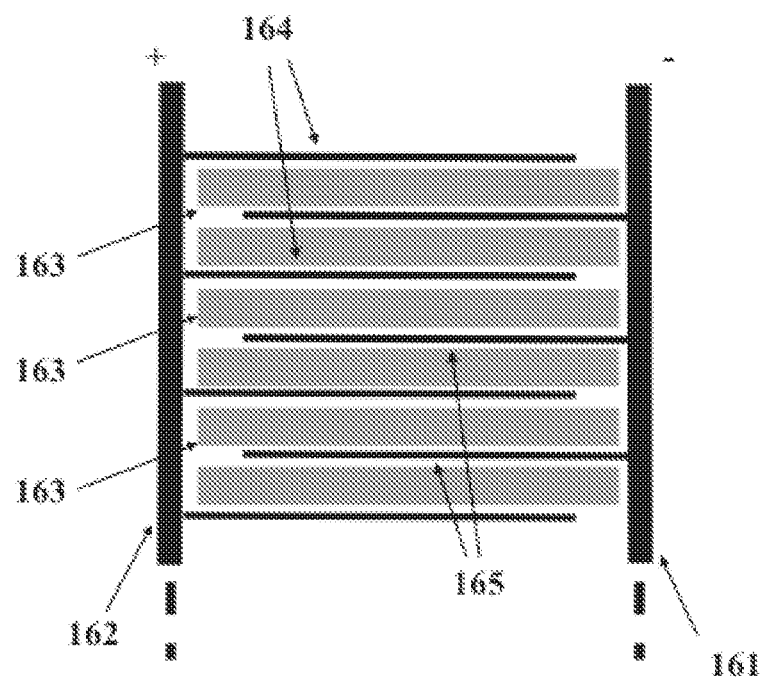
FIG. 15 schematically illustrates an exemplary multi layered electro-active polymer actuator, according to some embodiments of the present invention

FIG. 15 schematically illustrate an example of a multiple layer actuator. The EAP film (163) has a layer of conductor from each side (164 & 165). The conductive layers (164) are connected to a common conductor (162) which is connected to the positive node of the control box, and The conductive layers (165) are connected to a common conductor (161) which is connected to the negative node of the control box.

Figure 16A:
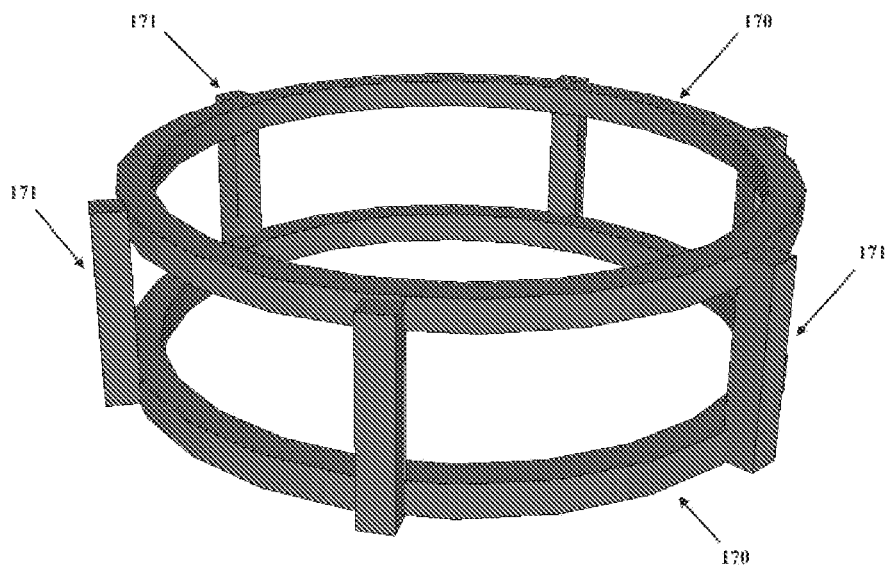
FIGS. 16A-16C are snapshots that schematically illustrate examples of an external design of a mechanism which holds an EAP film in a pre-stretched state, according to some embodiments of the present invention.
Figure 16B:
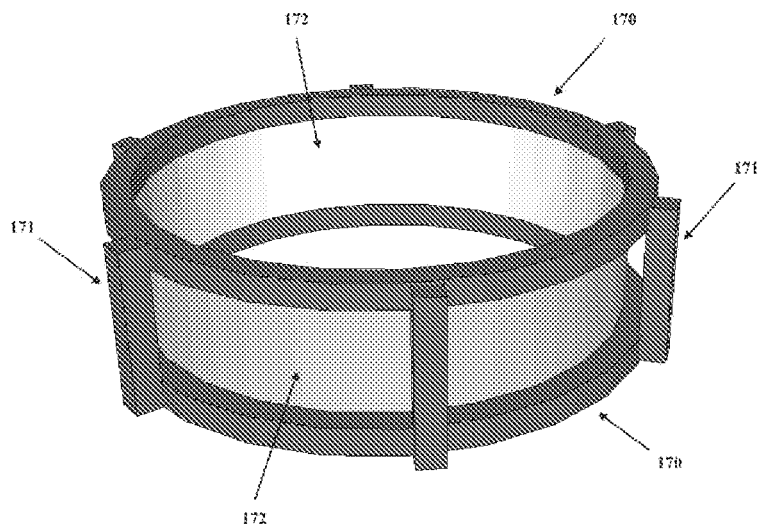
Figure 16C:
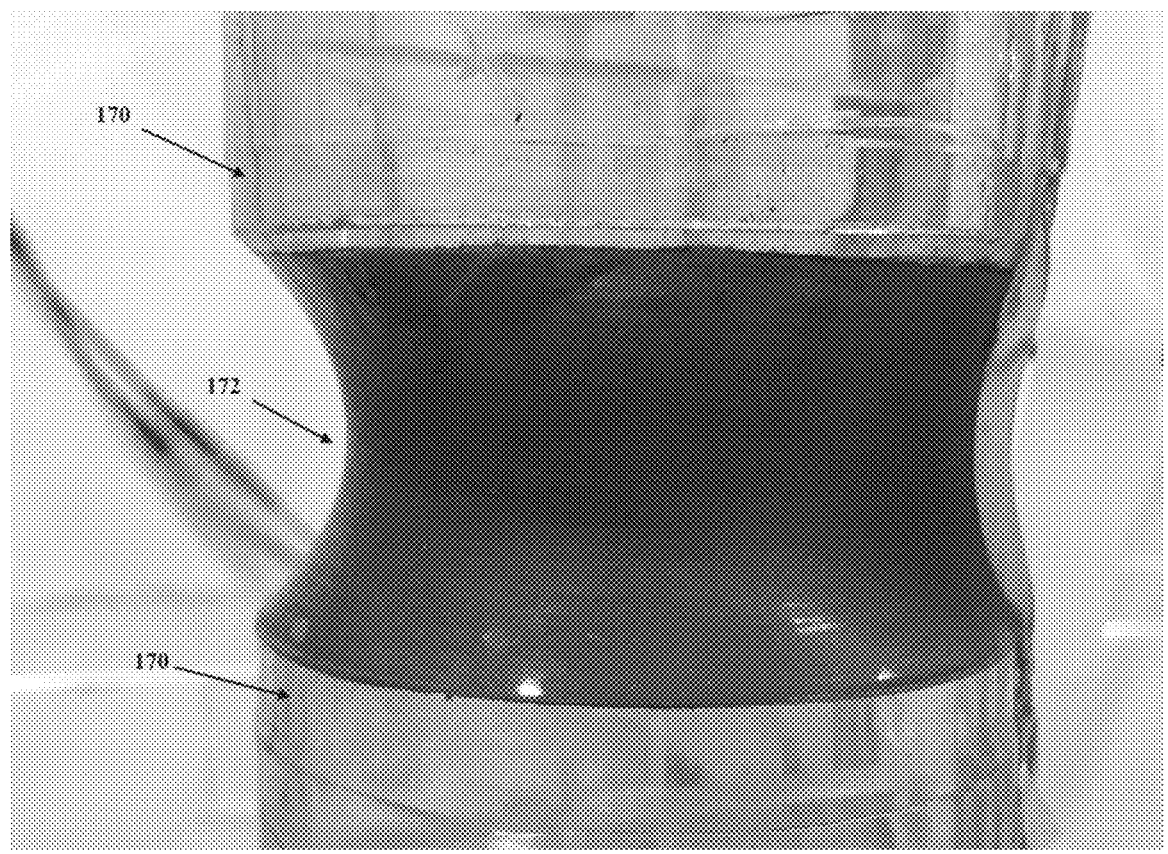

FIGS. 16A-16B schematically illustrate an example of two solid circular frames (170), which are held at a distance from each other using spacers (171). A pre-stretched EAP film (172) is held by the rings (170), and fixed in a pre-stretched state. The fixed pre-stretched EAP film, becomes curved in the gap between the solid rings, as see in FIG. 16C. Electrical activation of the EAP film, creates contraction in a radial direction.

All the above description and examples have been given for the purpose of illustration and are not intended to limiting in any way. Many different mechanism(s) and modification(s) may become apparent to those of ordinary skill in the art.

What is claimed is:

1. A method, comprising:
   fixing an electro-active polymer film in a pre-stretched state, wherein the electro-active polymer film has been pre-stretched in at least one planar stretch direction;
   wherein the fixing comprises:
      attaching at least one stretchable conductor to at least one surface of the pre-stretched electro-active polymer film and
      wrapping the pre-stretched electro-active polymer film with the at least one stretchable conductor around a solid body to form a fixed pre-stretched electro-active polymer film,
      wherein the fixed pre-stretched electro-active polymer film is configured to:
         a) apply a pressure to the solid body during a first time period when no current is being applied to the at least one stretchable conductor, and
         b) relieve the pressure on the solid body during a second time period when the current is being applied to the at least one stretchable conductor;
   coupling a pair of mechanical connectors at each end of at least one active region of the fixed pre-stretched electro-active polymer film; and
   connecting a control box to the fixed pre-stretched electro-active polymer film,
      wherein the control box is configured to apply the current to the at least one stretchable conductor during the second time period so as to obtain the fixed pre-stretched electro-active polymer film in the second condition.

2. The method of claim 1, further comprising: folding or attaching multiple layers of the fixed pre-stretched electro-active polymer X times, wherein X is between 2 and 10,000.

3. The method of claim 1, wherein the at least one stretchable conductor is made from carbon black based solution or solvent.

4. The method of claim 1, wherein the electro-active polymer film is pre-stretched in a biaxial planar stretch direction.

5. The method of claim 1, wherein the fixed pre-stretched electro-active polymer film is pre-stretched from 10% to 5000% of an original size of the electro-active polymer film.

6. The method of claim 1, wherein the fixed pre-stretched electro-active polymer film is pre-stretched from 100% to 5000% of an original size of the electro-active polymer film.

7. The method of claim 1, wherein a thickness of the electro-active polymer film is 10 μm to 5 mm.

8. The method of claim 1, wherein a thickness of the electro-active polymer film is 100 μm to 5 mm.

9. The method of claim 1, wherein a thickness of the electro-active polymer film is 100 μm to 1 mm.

10. The method of claim 1, wherein the at least one stretchable conductor comprises a network of gold and/or carbon nanoparticles embedded in elastic polyurethane.

11. The method of claim 1, wherein the at least one stretchable conductor comprises a layer of carbon black powder.

12. The method of claim 1, wherein the at least one stretchable conductor comprises a conducting polymer.

13. The method of claim 1, wherein the at least one stretchable conductor comprises a conducting rubber.

14. The method of claim 1, wherein the at least one stretchable conductor is attached to the at least one surface of the pre-stretched electro-active polymer film, by at least one of printing, etching, brushing, water dispersion, gluing, or any combination thereof.

15. The method of claim 1, wherein the at least one stretchable conductor comprises at least one of a network of gold or carbon nano-particles embedded in elastic polyurethane, a carbon graphite powder with silicon oil, a conducting silicon grease, a polyaniline solution, a carbon black powder, a conducting polymer, a conductive rubber, or any combination thereof.

16. The method of claim 1, wherein the control box comprises at least a battery and an electrical circuit.

17. The method of claim 16, wherein the electrical circuit is configured to transform a battery output voltage to a voltage required for the fixed pre-stretched electro-active polymer film to achieve the second condition.

18. The method of claim 17, wherein the electrical circuit is configured to activate and deactivate the fixed pre-stretched electro-active polymer film by applying a voltage according to a pre-determined sequence.

19. The method of claim 18, wherein the voltage applied to the fixed pre-stretched electro-active polymer film is from 10V to 20,000V.

20. The method of claim 1, further comprising:

measuring at least one of an electric charge or a capacitance during at least one of the first time period, the second time period, or any combination thereof, to monitor a strain feedback for at least one active region of the fixed pre-stretched electro-active polymer film.

* * * * *